US012141964B2

(12) United States Patent
DaCosta et al.

(10) Patent No.: US 12,141,964 B2
(45) Date of Patent: Nov. 12, 2024

(54) SYSTEMS, METHODS, AND DEVICES FOR THREE-DIMENSIONAL IMAGING, MEASUREMENT, AND DISPLAY OF WOUNDS AND TISSUE SPECIMENS

(71) Applicant: UNIVERSITY HEALTH NETWORK, Toronto (CA)

(72) Inventors: Ralph S. DaCosta, Etobicoke (CA); Danielle Dunham, Scarborough (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 549 days.

(21) Appl. No.: 17/423,449

(22) PCT Filed: Jan. 17, 2020

(86) PCT No.: PCT/IB2020/050380
§ 371 (c)(1),
(2) Date: Jul. 15, 2021

(87) PCT Pub. No.: WO2020/148721
PCT Pub. Date: Jul. 23, 2020

(65) Prior Publication Data
US 2022/0092770 A1 Mar. 24, 2022

Related U.S. Application Data

(60) Provisional application No. 62/793,837, filed on Jan. 17, 2019.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0035* (2013.01); *A61B 5/0071* (2013.01);
(Continued)

(58) Field of Classification Search
CPC ............... G06T 7/0012; G06T 7/33; G06T 2207/10028; G06T 2207/10048;
(Continued)

(56) References Cited

U.S. PATENT DOCUMENTS 5,971,918 A 10/1999 Zanger
6,678,398 B2 1/2004 Wolters et al.
(Continued)

FOREIGN PATENT DOCUMENTS

CN 102027434 4/2011
CN 102099671 6/2011
(Continued)

OTHER PUBLICATIONS

Office Action dated Jun. 29, 2022 in related CA application No. 2,955,976.
(Continued)

*Primary Examiner* — Md K Talukder
(74) *Attorney, Agent, or Firm* — JONES ROBB, PLLC

(57) ABSTRACT

The present disclosure provides methods, systems, and devices for coregistering imaging data to form three-dimensional superimposed images of a biological target such as a wound, a tumor, or a surgical bed. A three-dimensional map can be generated by projecting infrared radiation at a target area, receiving reflected infrared radiation, and measuring depth of the target area. A three-dimensional white light image can be created from a captured two-dimensional white light image and the three-dimensional map. A three-dimensional fluorescence image can be created from a captured two-dimensional fluorescence image and the three-dimensional map. The three-dimensional white light image and the three-dimensional fluorescence image can be aligned using one or more fiducial markers to form a three-dimensional superimposed image. The superimposed image can be
(Continued)

used to track wound healing and to excise cancerous tissues, for example, breast tumors. Images can be in the form of videos.

30 Claims, 25 Drawing Sheets

(51) Int. Cl.
  *G06T 7/33* (2017.01)
  *G16H 30/40* (2018.01)
(52) U.S. Cl.
  CPC .......... *A61B 5/0073* (2013.01); *A61B 5/0091* (2013.01); *A61B 5/445* (2013.01); *A61B 5/4842* (2013.01); *A61B 5/7425* (2013.01); *G06T 7/33* (2017.01); *G16H 30/40* (2018.01); *A61B 2576/02* (2013.01); *G06T 2207/10028* (2013.01); *G06T 2207/10048* (2013.01); *G06T 2207/10064* (2013.01); *G06T 2207/30024* (2013.01); *G06T 2207/30068* (2013.01); *G06T 2207/30088* (2013.01); *G06T 2207/30096* (2013.01); *G06T 2207/30204* (2013.01)
(58) Field of Classification Search
  CPC . G06T 2207/10064; G06T 2207/30024; G06T 2207/30068; G06T 2207/30088; G06T 2207/30096; G06T 2207/30204; A61B 5/0035; A61B 5/0071; A61B 5/0073; A61B 5/0091; A61B 5/445; A61B 5/4842; A61B 5/7425; A61B 2576/02; A61B 5/1079; A61B 5/0036; A61B 5/1073; A61B 5/1075; G16H 30/40; G01B 11/2513; G01B 11/245; G01S 17/86; G01S 17/46; G01S 17/894; G01S 17/89
  See application file for complete search history.

(56) References Cited

U.S. PATENT DOCUMENTS

| | | | |
|---|---|---|---|
| 8,620,410 | B2 | 12/2013 | Frangioni |
| 9,326,666 | B2 | 5/2016 | Frangioni |
| 9,340,490 | B2 | 5/2016 | Okura et al. |
| 9,743,836 | B2 | 8/2017 | Tsubouchi et al. |
| 2005/0288594 | A1 | 12/2005 | Lewkowicz et al. |
| 2006/0249689 | A1 | 11/2006 | Eustergerling et al. |
| 2010/0145419 | A1 | 6/2010 | Fraval |
| 2010/0292580 | A1 | 11/2010 | Gilhuly et al. |
| 2011/0275900 | A1 | 11/2011 | Gilhuly et al. |
| 2012/0007950 | A1* | 1/2012 | Yang .................. G06T 7/50 348/43 |
| 2012/0016230 | A1* | 1/2012 | Kishima ............. A61B 1/0646 600/425 |
| 2012/0051514 | A1 | 3/2012 | Sims et al. |
| 2013/0215235 | A1 | 8/2013 | Russell |
| 2013/0338479 | A1 | 12/2013 | Pogue et al. |
| 2014/0218720 | A1 | 8/2014 | Kindem |
| 2014/0378843 | A1* | 12/2014 | Valdes ................ A61B 1/063 600/476 |
| 2015/0030542 | A1 | 1/2015 | Singhal |
| 2015/0038837 | A1 | 2/2015 | Inoue et al. |
| 2015/0150460 | A1 | 6/2015 | Krishnaswamy et al. |
| 2016/0206202 | A1 | 7/2016 | Frangioni |
| 2016/0278678 | A1* | 9/2016 | Valdes ............... A61B 5/14546 |
| 2016/0377545 | A1 | 12/2016 | Wang |
| 2017/0059487 | A1 | 3/2017 | Wang |
| 2017/0085855 | A1 | 3/2017 | Roberts et al. |
| 2017/0235118 | A1 | 8/2017 | Kuster et al. |
| 2018/0114353 | A1 | 4/2018 | Champion et al. |
| 2018/0160047 | A1 | 6/2018 | Price et al. |
| 2018/0218508 | A1 | 8/2018 | Lee et al. |
| 2018/0242848 | A1 | 8/2018 | Dacosta et al. |
| 2018/0252909 | A1 | 9/2018 | Regensburger et al. |
| 2018/0276814 | A1 | 9/2018 | Frangioni |
| 2018/0279864 | A1 | 10/2018 | Frangioni |
| 2018/0325377 | A1 | 11/2018 | Dacosta et al. |
| 2019/0079011 | A1 | 3/2019 | Frangioni |
| 2019/0259162 | A1 | 8/2019 | Sartor |
| 2021/0051514 | A1 | 2/2021 | Li et al. |
| 2022/0092770 | A1* | 3/2022 | DaCosta ................ G01S 17/86 |
| 2023/0067762 | A1* | 3/2023 | Irrgang ................ H04N 13/246 |
| 2023/0280577 | A1* | 9/2023 | Valdes ................ A61B 5/0071 600/476 |
| 2024/0197241 | A1 | 6/2024 | Barclay et al. |

FOREIGN PATENT DOCUMENTS

| | | |
|---|---|---|
| CN | 102314707 | 1/2012 |
| CN | 102370462 | 3/2012 |
| CN | 106803284 | 6/2017 |
| CN | 107093171 | 8/2017 |
| CN | 107851176 | 3/2018 |
| EP | 4322176 | 2/2024 |
| JP | 2012023492 | 2/2012 |
| WO | 2004025556 | 3/2004 |
| WO | 2010080611 | 7/2010 |
| WO | 2013184830 | 12/2013 |
| WO | 2016063949 | 4/2016 |
| WO | 2017082242 | 5/2017 |
| WO | 2017096137 | 6/2017 |

OTHER PUBLICATIONS

European Search Report dated Aug. 23, 2022 in related EP Application No. 20740945.9, 8 pages.
European Search Report dated Aug. 31, 2022 in related EP Application No. 20741439.2, 8 pages.
Specification and Drawings filed Jul. 16, 2021 in related U.S. Appl. No. 17/423,597.
Office Action dated Dec. 6, 2022 in related CA Application No. 3,126,984.
Office Action dated Sep. 28, 2023 in related U.S. Appl. No. 17/423,597, 29 pages.
Office Action dated Sep. 26, 2023 received in related JP Application No. 2021-541476.
Office Action dated Sep. 20, 2023 received in related CN Application No. 2020800219629.
International Search Report and Written Opinion from International Application No. PCT/IB2020/050380, dated May 14, 2020.
International Search Report and Written Opinion from International Application No. PCT/IB2020/050381, dated May 26, 2020.
First Examination Report dated Mar. 24, 2023 in related IN App No. 202117030691.
Written Opinion dated Apr. 3, 2023 in related Application No. 11202107280U.
Examination Report dated Apr. 8, 2024 received in related SG Application No. 11202107280U.
Office Action dated Mar. 28, 2024 received in related CA Application No. 3,127,030.
Office Action dated Apr. 9, 2024 received in related JP Application No. 2021-541476.
European Search Report dated Feb. 15, 2024 received in related EP Application No. 23203744.0.
Office Action dated Mar. 26, 2024 received in related EP Application No. 20740945.9.
Notice of Allowance dated Jun. 10, 2024 in related U.S. Appl. No. 17/423,597.
Office Action dated Jun. 10, 2024 received in related Application No. MX/a/2021/008454.
Notice of Issuance dated Jun. 17, 2024 received in related CN Application No. 2020800219629.

\* cited by examiner

SYSTEMS, METHODS, AND DEVICES FOR THREE-DIMENSIONAL IMAGING, MEASUREMENT, AND DISPLAY OF WOUNDS AND TISSUE SPECIMENS

CROSS REFERENCE TO RELATED APPLICATIONS

This application is a U.S. national stage application under 35 U.S.C. § 371(c) of International Application No. PCT/IB2020/050380, filed Jan. 17, 2020, which claims priority to U.S. Provisional Patent Application No. 62/793,837, filed Jan. 17, 2019, the entire content of each of which is incorporated herein by reference.

TECHNICAL FIELD

The present disclosure relates to systems for and methods of coregistering multimodal image data to create three-dimensional representations.

INTRODUCTION

Wounds manifest themselves in a wide range of patient populations. Although wounds can be the result of a myriad of different causes from sudden traumatic injury to more gradual causes such as prolonged bedrest and metabolic conditions, one of their main commonalities and issues can be accurate characterization. Traditionally, wounds have been characterized by sight alone, which provides relatively little information regarding the number and types of cells populating the wound bed. Even if an imaging device is employed, the images obtained are usually two-dimensional. A two-dimensional image can be quite restrictive in assessing wound healing because a wound can maintain a relatively constant planar area while undergoing significant changes in depth. Improved characterization of wounds would help a clinician better understand whether a given treatment is working and better identify which treatments would have the greatest efficacy for a particular wound.

Accurately identifying tumor margins on a lumpectomy or mastectomy (breast) surgical sample, as well as the corresponding surgical bed, remains a major problem in breast conservative surgery. Identifying the exact location of residual tumor tissues in the surgical bed when positive margins are found on the surgical sample also remains a challenge. Conventional approaches are suboptimal and are not performed in real time in the operating room. For example, conventionally, if a surgical sample has a positive margin, the surgeon removes the corresponding tumor in the surgical bed by shaving off substantially thick and laterally extensive layers of tissue in order to achieve negative margins. This imprecise procedure reduces the chances of preserving sufficient healthy breast tissue, making the conservation effort difficult. Similar issues exist for other cancers and procedures, for example, removal of melanoma. Characterization of tissue damage and pathologies, for example, wounds, as well as removal of tissues generally are in need of improved tools and techniques for greater precision and accuracy.

SUMMARY

The present disclosure may solve one or more of the above-mentioned problems and/or may demonstrate one or more of the above-mentioned desirable features. Other features and/or advantages may become apparent from the description that follows.

In accordance with the present disclosure, a method of generating a three-dimensional image of a target using two-dimensional images is provided. The method can comprise, for example, the following. A three-dimensional map of a target area associated with one or more fiducial markers can be generated. A two-dimensional white light image of the target area and the fiducial markers can be captured. A three-dimensional white light image can be created from the two-dimensional white light image and the three-dimensional map. A two-dimensional fluorescence image of the target area and the fiducial markers can be captured. A three-dimensional fluorescence image can be created from the two-dimensional fluorescence image and the three-dimensional map. The three-dimensional white light image and the three-dimensional fluorescence image can be aligned using the fiducial markers to form a three-dimensional superimposed image.

In accordance with an aspect of the present disclosure, an imaging device is provided. The imaging device can comprise one or more of the following components. An excitation light source can be configured to emit a first radiation capable of exciting a fluorophore. A filter can be configured to prevent passage of reflected excitation light and permit passage of fluorescence emitted by the fluorophore. An imaging lens can be configured to focus radiation. A visible light source can be configured to emit a second radiation. An infrared light source can be configured to emit a third radiation. At least one image sensor can be configured to detect radiation. A processor can be configured to receive the detected radiation and to output data associated with the detected radiation. The imaging device can be configured to be handheld. The imaging device can be used to perform any of the methods described herein.

In accordance with an aspect of the present disclosure, an imaging device is provided. The imaging device can comprise one or more of the following components. An excitation light source can be configured to emit a first radiation capable of exciting a fluorophore. A filter can be configured to prevent passage of reflected excitation light and permit passage of fluorescence emitted by the fluorophore. An imaging lens can be configured to focus radiation. A visible light source can be configured to emit a second radiation. An infrared light source can be configured to emit a third radiation. At least one image sensor can be configured to detect radiation. A processor can be configured to receive the detected radiation and to output data associated with the detected radiation. The imaging device can be configured to be handheld.

In accordance with an aspect of the present disclosure, a system for three-dimensional fluorescence-based imaging of a target is provided. The system can comprise one or more of the following components, one or more of the components described for the imaging device, or both. At least one excitation light source can be configured to uniformly illuminate a target surface with a uniform field of excitation light during fluorescent imaging. At least one white-light source can be configured to illuminate the target surface during white light imaging. At least one infrared radiation source can be configured to emit infrared radiation toward the target surface. An image sensor can detect fluorescence, reflected radiation, or both. A filter can be configured to permit optical signals responsive to illumination of the target surface with the excitation light and having a wavelength corresponding to one or more of bacterial autofluorescence, tissue autofluorescence, and exogenously induced fluorescence to pass through the filter to the image sensor. A processor can be configured to, for example, perform one or more of the following. The processor can receive optical signals responsive to illumination of the target with the infrared light and, based on the received signals responsive to illumination of the target with the infrared light. The processor can generate a three-dimensional map of the target surface. The processor can receive detected optical signals responsive to illumination of the target surface with excitation light and generate a two-dimensional fluorescence image of the target surface. The processor can receive optical signals responsive to white light illumination of the target surface and generate a two-dimensional white light image of the target surface, and the processor can combine the three-dimensional map, the fluorescence image, and the white light image to generate a three-dimensional image of the target surface.

In accordance with an aspect of the present disclosure, a computer program product for use with the imaging device is provided. The computer program product can comprise a non-transitory computer readable medium. The non-transitory computer readable medium can store a computer program code for image processing. The computer program code can be executable by the processor in the imaging device to perform one or more of the methods described herein.

Additional objects and advantages of the present disclosure are set forth in part in the description which follows, and in part will be apparent from the description, or can be learned by practice of the present disclosure. The objects and advantages of the present disclosure can be achieved by means of the elements and combinations particularly pointed out in the appended claims.

Both the foregoing general description and the following detailed description are exemplary and explanatory only and are not restrictive of the present disclosure, as claimed.

The accompanying drawings, which are incorporated in and constitute a part of this specification, illustrate one (several) embodiment(s) of the present disclosure and together with the description, serve to explain the principles of the present disclosure.

DETAILED DESCRIPTION

The present disclosure enables the creation of three-dimensional images of an object that help a user better characterize and understand the object to achieve goals not previously possible or to more effectively achieve those goals than before. Image types that carry unique information can be combined in a manner that aids the user in visualizing a problem to more easily find a solution. Fluorescence images that carry information about the location of infected or cancerous tissue when placed in the direct context of a white light image can help a surgeon to more accurately remove affected tissue and minimize the need to operate again by showing the surgeon the information carried by the fluorescence in a more familiar context. Further these images can be converted from two-dimensional to three-dimensional image for superimposition to guide the user in a model environment better approximating the actual object. Two-dimensional images can be converted to three-dimensional images by wrapping them around a three-dimensional map of the object. The three-dimensional map can take many forms, for example, a mesh, and can be generated using a variety of different techniques, for example, using infrared radiation and its interaction with the object.

While the object to be imaged can be a target area of a biological target, the object visualized is by no means limited to medical contexts. On the contrary, the methods, devices, systems, and programs of the present disclosure have applicability in a wide range of technological fields in which information provided by fluorescence is relevant, for example, in food safety, sanitization, security, cosmetics, agriculture, horticulture, medicinal areas, agriculture, veterinary fields, border customs, quality control, and forensics. Images can include one or more of single images, a continuous set of images, a discontinuous set of images, a set of images from a common perspective (angle), a set of images from different perspectives (angles), a set of images using the same imaging technology, a set of images using different imaging technologies, a set of time lapsed images, and a video. A video can comprise one or more sets of images.

Figure 38:
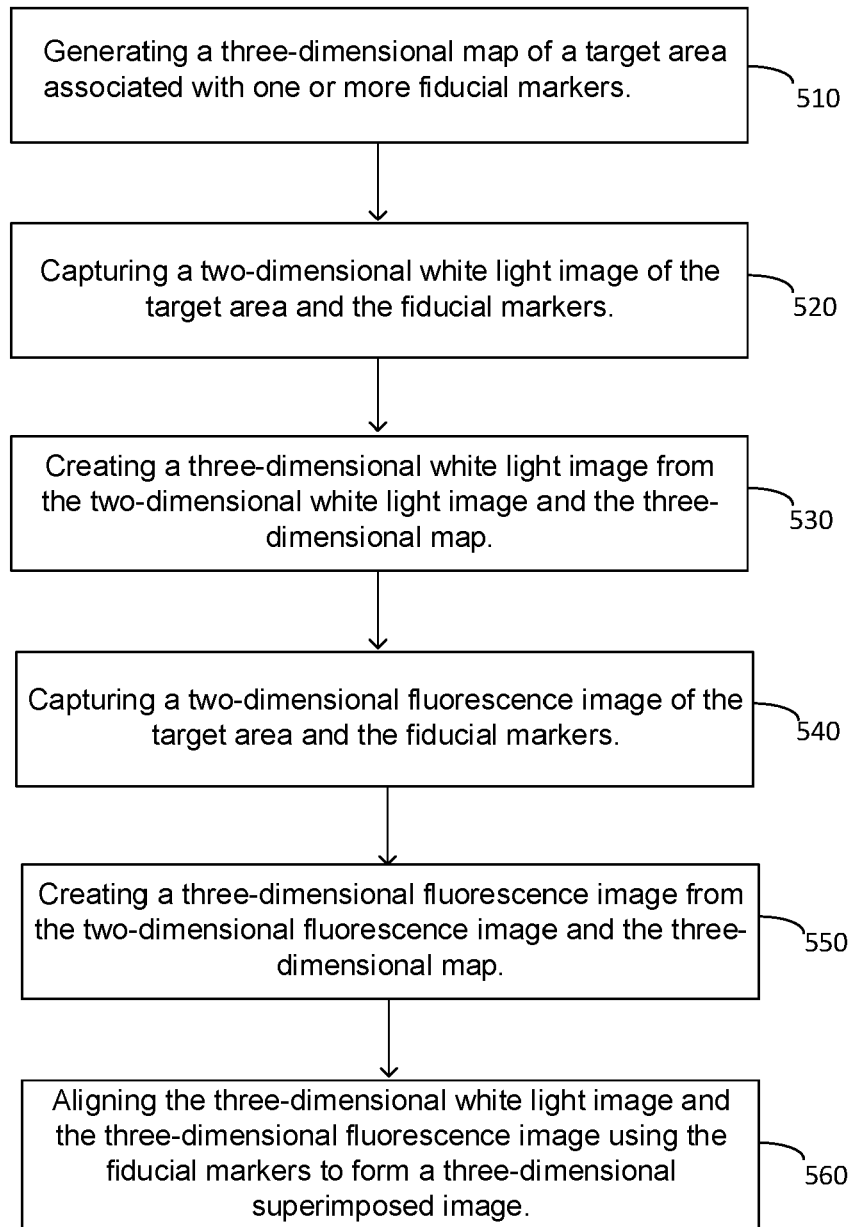
FIG. 38 is a flow chart depicting a method of the present disclosure.

In accordance with the present disclosure, a method of generating a three-dimensional image of a target using two-dimensional images is provided. The method can comprise, for example, the following. A three-dimensional map of a target area associated with one or more fiducial markers can be generated. A two-dimensional white light image of the target area and the fiducial markers can be captured. The white light image can be substituted with a single wavelength or a combination of wavelengths constituting a subset of visible light wavelengths. A three-dimensional white light image can be created from the two-dimensional white light image and the three-dimensional map. A two-dimensional fluorescence image of the target area and the fiducial markers can be captured. A three-dimensional fluorescence image can be created from the two-dimensional fluorescence image and the three-dimensional map. The three-dimensional white light image and the three-dimensional fluorescence image can be aligned using the fiducial markers to form a three-dimensional superimposed image. Examples of such steps designated as 510, 520, 530, 540, 550, and 560 are depicted in FIG. 38. The order of steps can be varied. Two-dimensional images can be superimposed and then collectively turned into a three-dimensional superimposed image using the three-dimensional map. The three-dimensional map can be in the form of a mesh.

Figures 39, 40:
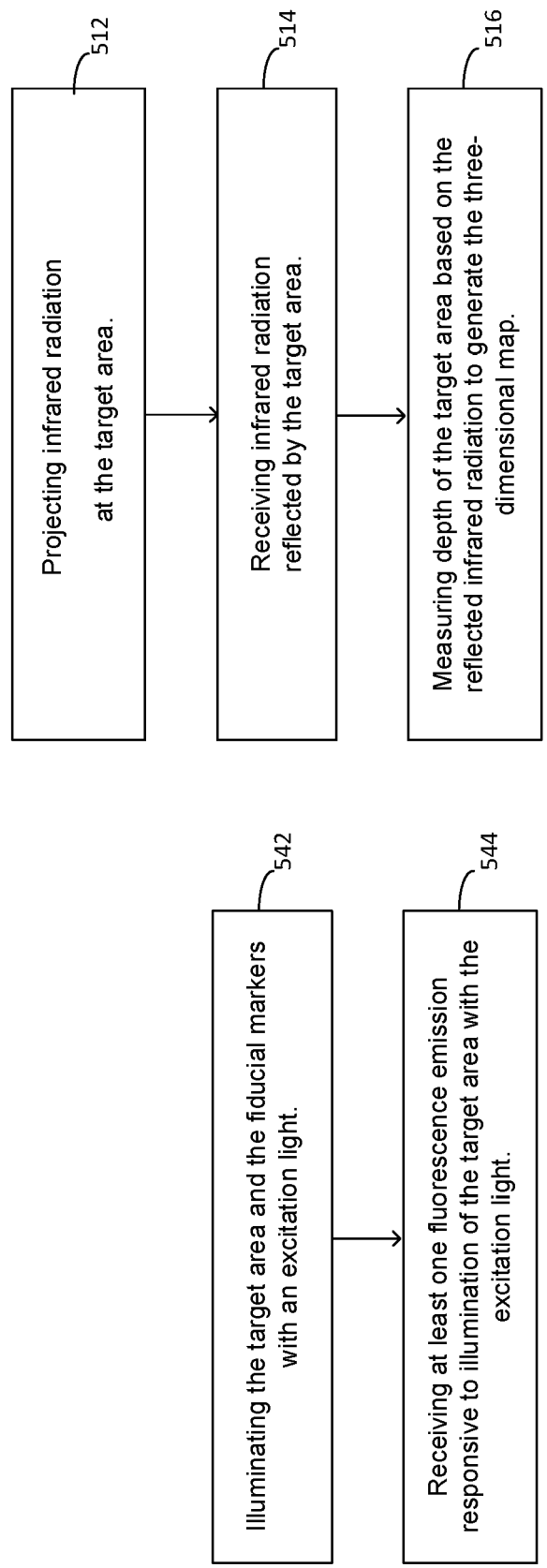
FIG. 39 is a flow chart depicting a method of the present disclosure.
FIG. 40 is a flow chart depicting a method of the present disclosure.

The capturing of the two-dimensional fluorescence image of the target area and the fiducial markers can be performed using any applicable technique. For example, the capturing can comprise illuminating the target area and the fiducial markers with an excitation light, and receiving at least one fluorescence emission responsive to illumination of the target area with the excitation light. Examples of such steps designated as 542 and 544 are depicted in FIG. 39. The excitation light can comprise one or more wavelengths. For example, the excitation light can be between about 400 nm and about 450 nm. A wavelength of about 405 nm is such an example. The capturing of the two-dimensional fluorescence image of the target area and the fiducial markers can comprise capturing an emission of at least one fluorescent molecule. The at least one fluorescent molecule can comprise an endogenous molecule capable of fluorescing. The at least one fluorescent molecule can comprise an endogenous molecule capable of fluorescing induced by an exogenous molecule. Induction can be brought about, for example, by accumulation, or modification, or both of the endogenous molecule. The at least one fluorescent molecule can comprise an exogenous molecule capable of fluorescing, a molecule comprising an exogenously added moiety capable of fluorescing, or both. For example, the at least one fluorescent molecule can comprise aminolevulinic acid (ALA) induced porphyrin.

The three-dimensional map can be generated using any appropriate technique or combination of techniques. For example, the three-dimensional map can be generated using infrared light. The three-dimensional map can be generated using near infrared light. For example, generating the three-dimensional map can comprise projecting infrared radiation at the target area, receiving infrared radiation reflected by the target area, and measuring depth of the target area based on the reflected infrared radiation to generate the three-dimensional map. Examples of such steps designated as 512, 514, and 516 are depicted in FIG. 40. The infrared radiation can be projected as a beam split into a light pattern. The reflected infrared radiation can comprise a distortion of the light pattern, and the depth can be measured based on the distortion of the light pattern. The light pattern can be formed by a diffraction grating. The light pattern can comprise a plurality of dots of any size, shape, or intensity, or combination thereof. Alternative methods of measuring depth can be employed. For example, the depth can be measured by time-of-flight based on a phase shift between the projected and the reflected infrared radiation.

In accordance with the present disclosure, the following steps can be performed. One or more fiducial markers can be placed inside, along, and/or outside a perimeter of a target area on a surface of a biological target. A three-dimensional map of the target area can be generated by projecting infrared radiation at the target area, receiving infrared radiation reflected by the target area, and measuring depth of the target area based on the reflected infrared radiation to generate the three-dimensional map. A two-dimensional white light image of the target area and the one or more fiducial markers can be captured. The white light image can be substituted or generated with a single wavelength of light or a combination of wavelengths of light constituting a subset of visible light wavelengths. A three-dimensional white light image can be created from the two-dimensional white light image and the three-dimensional map. A two-dimensional fluorescence image of the target area and the one or more fiducial markers can be captured. The fluorescence two-dimensional image capturing can comprise exposing the target area and the one or more fiducial markers to at least one wavelength capable of exciting at least one fluorescent molecule in the target area and receiving at least one fluorescence emission from the at least one fluorescent molecule in the target area through a filter. A three-dimensional fluorescence image can be created from the two-dimensional fluorescence image and the three-dimensional map. The three-dimensional white light image and the three-dimensional fluorescence image can be aligned using the one or more fiducial markers to form a three-dimensional superimposed image. The order of steps can be varied. Two-dimensional images can be superimposed and then collectively turned into a three-dimensional superimposed image using the three-dimensional map. The three-dimensional map can be in the form of a mesh.

The two-dimensional white light image, the two-dimensional fluorescence image, or any other image type described herein, can be captured using any suitable camera, imaging device, or image sensor. For example, the MoleculLight i:X imaging device available from MolecuLight Inc. of Toronto, Ontario, Canada, which includes a 5 megapixel camera, emits at 405 nm, and includes fluorescence emission filters of 500-545 nm and 600-665 nm respectively. An imaging device and associated methods described in U.S.

Pat. No. 9,042,967, which is incorporated by reference in its entirety, can be used. Alternatively, one of the devices disclosed in U.S. Provisional Patent Application No. 62/625,967, filed Feb. 2, 2018 and entitled "Devices, Systems, and Methods for Tumor Visualization and Removal," U.S. Provisional Patent Application No. 62/625,983, filed Feb. 3, 2018 and entitled "Devices, Systems, and Methods for Tumor Visualization and Removal," and/or PCT/CA2019/000015, filed Feb. 1, 2019, entitled "Devices, Systems, and Methods for Tumor Visualization and Removal" and published as WO2019/148,268 on Aug. 8, 2019, the entire content of each of which is incorporated herein by reference, may be used to capture white-light images and/or fluorescence images.

A charged-coupled display (CCD), complementary metal-oxide-semiconductor (CMOS), N-type metal-oxide-semiconductor (NMOS), quantum Image Sensor (QIQ), or other image sensor, or combination thereof can be employed in capturing the two-dimensional white-light image, two-dimensional fluorescence image, or any other type of image described herein. The image can be captured using artificial and/or natural ambient light, one or more dedicated light sources, or a combination thereof. For example, the image can be captured using flash photography.

The source of white light can be full or partial spectrum visible light. For example, the white light spectrum can be from about 380 nm to about 740 nm, from about 400 nm to about 700 nm, from about 425 nm to about 690 nm, from about 450 nm to about 680 nm, or any intermediate range thereof. The source of white light can be produced directly or initially as white light, formed from sources of different wavelengths, a source of a defined wavelength or range of wavelengths shifted, for example, using quantum dots (QDots), to multiple wavelength or a wider spectrum of wavelengths, or any combination thereof. The white image can be substituted with or complemented by a different type of image, for example, a monochromatic color image, an infrared image, or an ultraviolet image, or any combination thereof.

Infrared radiation can be produced, projected, and received using any appropriate technique, device, or combination thereof. The infrared radiation can be projected as a beam split into a light pattern, the reflected infrared radiation can comprise a distortion of the light pattern, and the depth can be measured based on the distortion of the light pattern. Thus, the infrared radiation can comprise structured light. The light pattern can be formed by a diffraction grating and the light pattern can comprise a plurality of dots. The depth measurement can be determined using triangulation. The aforementioned infrared depth imaging can be used in the Microsoft Kinect I system (Microsoft Corporation, Redmond, Washington). Unstructured infrared radiation can be used additionally or in the alternative to structured infrared radiation. The depth can be additionally or alternatively measured by one or more time-of-flight (ToF) sensors, for example, based on a phase shift between the projected and reflected infrared radiation. This type of infrared depth imaging can be used in the Microsoft Kinect II system. Any suitable infrared camera, sensor, or imaging device, or combination thereof can be used.

The projected and/or reflected infrared radiation can be from about 700 nm to about 1.0 mm, from about 750 nm to about 1.0 µm, from about 1.0 µm to about 1.25 µm, from about 1.25 µm to about 1.5 µm, from about 1.5 µm to about 5.0 µm, from about 5.0 µm to about 15.0 µm, from about 15.0 µm to about 50 µm, from about 50 µm to about 150 µm, from about 150 µm to about 250 µm, from about 250 µm to about 500 µm, from about 500 µm to about 750 µm, or from about 750 µm to about 1.0 mm, or an intermediate range thereof, or a combination thereof. The infrared imaging can be performed in near infrared (for example, from about 0.75 µm to about 1.4 µm), short wavelength infrared (for example, from about 1.4 µm to about 3.0 µm), medium wavelength infrared (for example, from about 3.0 µm to about 8.0 µm), long wavelength infrared (for example, from about 8.0 µm to about 15 µm), far (very long wavelength) infrared (for example, from about 8.0 µm to about 1.0 mm), or any combination thereof.

The white light source, the fluorescence excitation light source, the infrared light source, or any other relevant light source for use in the present disclosure can be of any appropriate design or combination of designs. The light source can be coherent or incoherent, collimated or uncollimated, focused or unfocused, polarized or unpolarized, or any combination thereof. A light beam angle of less than about 1 degree, from about 1 degree to about 5 degrees, from about 5 degrees to about 15 degrees, from about 15 degrees to about 25 degrees, from about 25 degrees to about 35 degrees, from about 35 degrees to about 50 degrees, from about 50 degrees to about 75 degrees, from about 75 degrees to about 90 degrees, from about 90 degrees to about 120 degrees, from about 120 degrees to about 150 degrees, and from about 150 degrees to about 180 degrees can be used as the white light or other light source. One or more lasers and/or light emitting diodes (LED) can be used. A candescent, thermal, arc, incandescent, fluorescent, semiconductor-based, sodium vapor, or mercury vapor, or any combination or number thereof can be used as the light source. A single or multiple light source can be used. An array of light sources can be used.

The distance of the light source to the target to be imaged and/or measured can be, for example, from about 1.0 mm to about 10 m, from about 0.5 cm to about 5.0 m, from about 1.0 cm to about 2.5 m, from about 2.5 cm to about 1.0 m, from about 5.0 cm to about 0.5 m, from about 10.0 cm to about 0.25 m, or from about 25 cm to about 100 cm, or any intermediate distance thereof, or any combination thereof from the target area. Any number or type of light sources can be used. The light sources can be fixed or movable. The light sources can be integrated into the same device housing the camera, detector, or other imaging device, and/or can be external to such a device. The light source can be located internal or external to a target area or target volume. The one or more light sources can be articulated (for example, manually) to vary the illumination angle and spot size on the imaged surface, for example by using a built-in pivot, and can be powered, for example, through an electrical connection to a wall outlet and/or a separate portable rechargeable battery pack.

The fluorescence excitation wavelength can be matched to an emission wavelength of the one or more fluorophores targeted by the imaging. For example, the excitation wavelength can be from about 300 nm to about 325 nm, from about 325 nm to about 350 nm, from about 350 nm to about 375 nm, from about 375 nm to about 400 nm, from about 400 nm to about 425 nm, from about 425 nm to about 450 nm, from about 450 nm to about 475 nm, from about 475 nm to about 500 nm, from about 500 nm to about 525 nm, from about 525 nm to about 550 nm, from about 550 nm to about 575 nm, from about 575 nm to about 600 nm, from about 600 nm to about 625 nm, from about 625 nm to about 650 nm, from about 675 nm to about 700 nm, from about 750 nm to about 775 nm, from about 775 nm to about 800 nm, from about 800 nm to about 825 nm, from about 825 nm to about 850 nm, from about 850 nm to about 875 nm, from about 875 nm to about 900 nm, or from about 900 nm to about 1.0 mm, or any intermediate or overlapping range thereof, or any combination thereof.

The at least one fluorescence excitation wavelength can comprise a wavelength of, for example, 405 nm, with a spread of about 0.0 nm, from about 0.01 nm to about 0.05 nm, from about 0.5 nm to about 1.0 nm, from about 1.0 nm to about 2.5 nm, from about 2.5 nm to about 7.5 nm, from about 10 nm to about 25 nm, or from about 15 nm to about 30 nm, or an intermediate spread, or a combination thereof. The imaging device can use, for example, two violet/blue light (for example, 405 nm+/−10 nm emission, narrow emission spectrum) LED arrays (Opto Diode Corporation, Newbury Park, California), each situated on either side of the imaging detector assembly as the excitation or illumination light sources. These arrays have, for example, an output power of approximately 1 Watt each, emanating from a 2.5×2.5 cm² source, with a 70-degree illuminating beam angle. The LED arrays can be used to illuminate the tissue surface from a distance of about 10 cm, which means that the total optical power density on the skin surface can be about 0.08 W/cm².

The light signal produced by the light sources can be detected by the imaging device using one or more optical filters that reject the excitation light but allow selected wavelengths of emitted light from the tissue to be detected, thus forming an image on the display. Band-pass filters can be selected and aligned in front of a digital camera lens or other image detector or sensor to selectively detect specific optical signals from the target based on the wavelength of light desired. Spectral filtering of detected optical signals (for example, absorption, fluorescence, and/or reflectance) can also employ a liquid crystal tunable filter (LCTF), or an acousto-optic tunable filter (AOTF) that can be a solid-state electronically tunable spectral band-pass filter. Spectral filtering can also involve the use of continuous variable filters, and/or manual band-pass optical filters. These devices can be placed in front of the imaging detector to produce multispectral, hyperspectral, and/or wavelength-selective imaging of a target area.

Optical or variably oriented polarization filters (for example, linear or circular combined with the use of optical wave plates) can be attached to the one or more light sources and/or the imaging device, sensor, or camera. These filters can permit imaging with polarized light illumination and non-polarized light detection or vice versa, or polarized light illumination and polarized light detection, with either white light reflectance and/or fluorescence imaging.

A PrimeSense camera (technology available from Apple Inc. of Cupertino, California), components thereof, or other sensors capable of three-dimensional imaging can be used in the techniques of the present disclosure. The PrimeSense camera includes a Carmine 1.08 sensor, a Carmine 1.09 (short range) sensor, and a Capri 1.25 (embedded) sensor. Depth acquisition employs light coding technology. A scene can be scanned with near-infrared light. An infrared dot pattern can be emitted outward towards the target area. Light can be distorted when it contacts the target area and this distortion can be measured by the camera or other sensors, including, for example, a CMOS image sensor. An infrared camera sensor images the dot pattern on the target, simultaneously a white light RGB camera (adjacent to the infrared camera) captures a regular white light image of the target. The CMOS image sensor works with a visible video sensor to produce a depth map provided by PrimeSense System on a Chip (SoC)'s Carmine (PS1080) and Capri (PS1200) sensors that can be merged with a color image.

As an example, the PrimeSense device emits an (invisible to the naked eye) infrared dot pattern outward towards the target. An infrared camera sensor images the dot pattern on the target, simultaneously a white light RGB camera (adjacent to the infrared camera) captures a regular white light image of the target. The embedded software creates a "mesh" from the infrared dot pattern of the target topology. Then it wraps the white light image to that mesh topology using image (transforming function) morphing software code. The result is a white light image that can be transformed from two-dimensional to three-dimensional. The software used to run this process can be an open source software development kit (SDK) called OpenNI. Any appropriate software can be used, for example, OpenKinect or Microsoft Kinect Software Development Kit. A mesh or point cloud can also be created and manipulated using MeshLab.

In accordance with the present disclosure, a color image can alternatively or additionally be a fluorescence image. A registration process can be performed to align color image (RGB) and depth (D) information. The light coding infrared patterns can be deciphered in order to produce a VGA size depth image of the target area. The PrimeSense camera includes embedded software for image processing. Additional or alternative software can be employed. For example, open source SDK called OpenNI can be used. The embedded software creates a "mesh" from the infrared dot pattern of the target topology. Then it wraps the white light image to that mesh topology using image (transforming function) morphing software code. The result is a white light image that can be transformed from two-dimensional to three-dimensional. The PrimeSense camera can deliver visible video, depth, and audio information in a synchronized fashion via a USB 2.0 interface. An Xtion PRO LIVE camera (including an infrared dot projector, a RGB camera, and an infrared camera) available from ASUS Computer International (Fremont, California) can be used instead or in addition to a PrimeSense camera. A camera/sensor/projector system as described in U.S. Patent Application No. 2017/0054966, which is incorporated by reference in its entirety, can be used. Time-of-flight infrared imaging can be used instead or in addition to structured light-based infrared imaging for depth measurement to obtain three-dimensional coordinate information of a target area.

Prior to imaging, fiduciary markers (for example, using an indelible fluorescent ink pen) can be placed on the surface of the skin, or other relevant surface, near the biological target edges or perimeter. For example, four spots, each of a different fluorescent ink color from separate indelible fluorescent ink pens, which can be provided as a kit to the clinical operator, can be placed near the target area margin or boundary on the normal skin surface. These colors can be imaged by the device using the excitation light and a multispectral band filter that matches the emission wavelength of the four ink spots. Image analysis can then be performed, by co-registering the fiduciary markers for inter-image alignment. This technique can facilitate longitudinal, time-sequence imaging of target areas, and the clinical operator can therefore image a target area over time without need for aligning the imaging device during every image acquisition.

To aid in intensity calibration of the fluorescence images, a disposable simple fluorescent standard 'strip' can be placed into the field of view during target area imaging (for example, by using a mild adhesive that sticks the strip to the skin temporarily). The strip can be impregnated with one or several different fluorescent dyes of varying concentrations which can produce pre-determined and calibrated fluorescence intensities when illuminated by the excitation light source, which can have single (for example, 405 nm) or multiple fluorescence emission wavelengths or wavelength bands for image intensity calibration. The disposable strip can also have the four spots as described above (for example, each of different diameters or sizes and each of a different fluorescent ink color with a unique black dot placed next to it) from separate indelible fluorescent ink pens. With the strip placed near the target area margin or boundary on the normal skin surface, the device can be used to take white light and fluorescence images. The strip can offer a convenient way to take multiple images over time of a given target area and then align the images using image analysis. The fluorescent "intensity calibration" strip can also contain an added linear measuring apparatus, such as a ruler of fixed length to aid in spatial distance measurements of the target areas. Such a strip can be an example of a calibration target which can be used with the device to aid in calibration or measuring of image parameters (for example, target area size, fluorescence intensity, and the like). Other similar or functionally equivalent calibration targets can be used additionally or in the alternative.

The one or more fiducial markers can comprise fluorescent fiducial markers. For example, the fluorescent fiducial markers can comprise fluorescein. The at least one fluorescent molecule can comprise an endogenous molecule capable of fluorescing, an exogenous molecule capable of fluorescing, or both. The at least one fluorescent molecule can comprise an endogenous molecule capable of fluorescing induced by an exogenous molecule. Induction can be brought about, for example, by accumulation, or modification, or both of the endogenous molecule. The at least one fluorescent molecule can comprise an exogenous molecule capable of fluorescing or a molecule comprising an exogenously added moiety capable of fluorescing. In an example, indocyanine green (ICG) can be excited at about 760 nm, at about 780 nm, or both. A filter comprising a notch from about 657 nm to about 825 nm can be used for 760 nm excitation. A filter comprising a notch from about 690 nm and about 840 nm can be used for 780 nm excitation.

The techniques described herein can detect a portion, a majority, or essentially all tissue autofluorescence (AF). For example, using a multi-spectral band filter, tissue autofluorescence can be measured emanating from various tissue biomolecules, as well as blood-associated optical absorption, for example under 405 nm excitation: collagen (Types I, II, III, IV, V and others) which appear green, elastin which appears greenish-yellow-orange, reduced nicotinamide adenine dinucleotide (NADH), flavin adenine dinucleotide (FAD), which emit a blue-green autofluorescence signal, and bacteria/microorganisms, most of which can appear to have a broad (for example, green and red) autofluorescence emission. Image analysis can include calculating a ratio of red-to-green AF in the image. Intensity calculations can be obtained from regions of interest within the target area images. Pseudo-colored images can be mapped onto the white light images of the target area.

The techniques of the present disclosure can be used in conjunction with exogenous "pro-drug" agents, including, but not limited to, ALA, to increase the endogenous production of porphyrins in bacteria/microorganisms and thereby increase the intensities of unique 'porphyrin' fluorescence signals emanating from these bacteria to improve the detection sensitivity and specificity of the device. Thus, the techniques can be used to conveniently image photosensitizer-induced fluorescence (for example, PpIX) in bacteria, growing in culture or in patients' wounds for subsequent image-guided targeted swabbing/biopsy or treatment, for example using photodynamic therapy (PDT) or hyperbaric oxygen therapy (HOT). The techniques when used with for example consumable, commercially available fluorescence contrast agents can increase the signal-to-background for sensitive detection of bacteria, in and around target areas.

The at least one fluorescent molecule can comprise an induced endogenous fluorescent molecule, for example, aminolevulinic acid (ALA) induced porphyrins. ALA can be topically administered to the target area, and imaging can be performed 1-3 hours later for enhanced red fluorescence of target area bacteria. The pro-drug aminolaevulinic acid (ALA) induces porphyrin formation in almost all living cells. Many bacteria species exposed to ALA are able to induce protoporphyrin IX (PpIX) fluorescence. The use of ultra-low dose ALA can induce PpIX formation in the bacteria and hence can increase the red fluorescence emission, which can enhance the red-to-green fluorescence contrast of the bacteria imaged with the device. ALA is non-fluorescent by itself, but PpIX is fluorescent at around 630 nm, 680 and 710 nm, with the 630 nm emission being the strongest. The imaging device can then be used to image the green and red fluorescence from the target area and the surrounding tissues.

A clinical operator can premix the ALA, which is usually provided commercially in lyophilized form with physiological saline or other type of commercially available cream/ointment/hydrogel/dressing and the like, at a given dose and administer the agent topically by spraying it, pouring it, or carefully applying the agent to the target area prior to imaging. Approximately 10-30 minutes afterwards, although this time can vary, fluorescence imaging can be performed in a dimly lit or dark room. Bacteria under white light and perhaps poorly autofluorescent can appear as bright red fluorescent areas in and around the target area. The fluorescence images can be used to direct targeted swabbing, biopsy and/or fine needle aspirates of the target area for bacterial culturing based on the unique bacterial fluorescence signal. This procedure can be performed at different depths, for superficial and deep wounds.

Suitable exogenous optical molecular targeting probes can be prepared using commercially available fluorescence labeling kits, such as the Alexa Fluor active esters and kits (for example, Zenon Antibody Labeling Kits and or EnzChek Protease Assay Kits, Invitrogen) for labeling proteins, monoclonal antibodies, nucleic acids and oligonucleotides (Invitrogen). For example, these fluorescent dye bioconjugates cover the following wavelength ranges: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 dyes, where the number stated refers to the excitation wavelength of the dye. These kits can offer well-differentiated fluorescence emission spectra, providing many options for multicolor fluorescence detection and fluorescence resonance energy transfer, based on the appropriate selection of fluorescence emission filters with the imaging device. The fluorescence dyes can offer high absorbance at wavelengths of maximal output of common excitation sources. They can be bright and unusually photostable to assist in achieving fluorescence of their bioconjugates. The dyes can offer good water solubility for ease of conjugation within the clinical exam room and resistance of the resulting conjugates to precipitation and aggregation. The fluorescence spectra of the dyes can be insensitive to pH over a broad range, which makes them particularly useful for wound imaging, because wound pH can vary. In addition, other commercial or non-commercial fluorescent agents exist which can be appropriate for biological imaging of wounds and can be combined with the described device, including fluorescent blood pooling agents and various wound-enzyme or protease activated probes from VisEn Medical (Boston, Mass., USA), for example.

These targeting fluorescent bioconjugates can be prepared using such labeling kits prior to the clinical exam of the target area using the imaging device in fluorescence mode. They can be stored in light-tight containers to avoid photobleaching. Such fluorescence bioconjugates can be prepared in solution at a known and appropriate concentration prior to fluorescence imaging of the target area using the device, and then administered/applied directly to the target area by one or more means, for example, topically (for example, via an aerosol or a spray), orally (for example, via a drink or lavage), or systemically (for example, via intravenous injection). Such dyes can target specific biological components depending on the targeting moiety, and can include, for example, one or more of bacteria, fungi, yeast, spores, virus, microbes, parasites, exudates, pH, blood vessels, reduced nicotinamide adenine dinucleotide (NADH), flavin adenine dinucleotide (FAD), microorganisms, specific types of connective tissues (for example, collagens, elastin), tissue components, vascular endothelial growth factor (VEGF), endothelial growth factor (EGF), epithelial growth factor, epithelial cell membrane antigen (ECMA), hypoxia inducible factor (HIF-1), carbonic anhydrase IX (CAIX), laminin, fibrin, fibronectin, fibroblast growth factor, transforming growth factors (TGF), fibroblast activation protein (FAP), enzymes (for example, caspases, matrix metalloproteinases (MMPs), and the like), tissue inhibitors of metalloproteinases (for example, TIMPs), nitric oxide synthase (NOS), inducible and endothelial NOS, lysosomes in cells, macrophages, neutrophils, lymphocytes, hepatocyte growth factor (HGF), anti-neuropeptides, neutral endopeptidase (NEP), granulocyte-macrophage colony stimulating factor (GM-CSF), neutrophil elastases, cathepsins, arginases, fibroblasts, endothelial cells, keratinocytes, keratinocyte growth factor (KGF), macrophage inflammatory protein-2 (MIP-2), macrophage inflammatory protein-2 (MIP-2), macrophage chemoattractant protein-1 (MCP-1), polymorphonuclear neutrophils (PMN) and macrophages, myofibroblasts, interleukin-1 (IL-1) and tumor necrosis factor (TNF), nitric oxide (NO) (Kit from Calbiochem, Model DAF-2 DA), c-myc, beta-catenin, and circulating endothelial progenitor cells (EPCs) from the bone marrow. Exogenous optical agents can include, for example, one or more of activated molecular beacons (for example, targeted), nanoparticles having fluorescent agents (for example, labeled on the surface and/or containing or carrying fluorescent agents), and scattering or absorbing nanoparticles (for example, gold, silver, and the like).

Commercially available organic fluorophores have properties that are dependent on hydrogen ion concentration, rendering them useful as probes for measuring pH, and they typically have pH sensitive UV/visible absorption properties. Commercially available pH sensitive fluorescent dyes employed in intracellular studies can provide a reduced fluorescent signal in acidic media or alternatively the pKa of the dye can be outside the intracellular pH window of between 5-8 pH units. However, other pH-sensitive fluorescent agents respond by increasing their fluorescence intensities. For example, Invitrogen Molecular Probes (Thermo Fisher Scientific) offers a variety of fluorescent pH indicators, their conjugates and other reagents for pH measurements in biological systems. Among these are several probes with unique optical response and specialized localization characteristics: for example, visible light-excitable SNARF pH indicators enable researchers to determine intracellular pH in the physiological range using dual-emission or dual-excitation ratiometric techniques, thus providing useful tools for confocal laser-scanning microscopy and flow cytometry. LysoSensor probes, as well as indicators based on the Oregon Green fluorophore, can be used to estimate the pH in a cell's acidic organelles. There are also fluorescent pH indicators coupled to dextrans that can be used. Following loading into cells, indicator dextrans can be well retained. Such fluorescent agents can be prepared in solution in advance at a known and appropriate concentration prior to fluorescence imaging of the target area using the device, and then administered/applied directly to the target area and surrounding normal tissues by one or more means, for example, topically (for example, via an aerosol or a spray), orally (for example, via a drink or lavage), or systemically (for example, via intravenous injection).

The target area can comprise at least one wound. The wound can be any type of wound. For example, the wound can comprise an abrasion, a laceration, a puncture, an avulsion, a bruise, a contusion, a bite, a burn, a rash, frostbite, a boil, a mole, a pimple, a cyst, an ulcer (such as a diabetic ulcer), a bed sore, or any combination thereof. The wound can be deep or superficial. A wound can be external on or in the skin, or internal on or in an internal membrane. The wound can comprise the epidermis, the dermis, or the hypodermis, or any combination thereof. The wound can be infected or uninfected. An infected wound can be infected with any kind, number, or combination of organisms. The infection can comprise one or more bacteria, one or more fungi, one or more protozoa, or one or more viruses, or any combination thereof. The organism can be monocellular, multicellular, or non-cellular.

The method can further comprise determining one or both of a surface area and a volume of the wound. The determination can be performed any appropriate number of times. For example, the method can be performed at least twice, the two performances comprising a first performance and a second performance separated by a chosen period, for example, at least one hour, at least three hours, at least one day, at least one week, at least one month, or the like. The interval between performances can be, for example, from 1 minute to about 10 minutes, from about 5 minutes to about 30 minutes, from about 30 minutes to about 3 hours, from about one hour to about six hours, from about six hours to about 12 hours, from about 12 hours to about one day, from about one day to about two days, from about two days to about one week, from about one week to about two weeks, from about two weeks to about one month, from about one month to about six weeks, from about six weeks to about three months, from about three months to about six months, or from about six months to about one year, or any intervening or overlapping time period, or a combination thereof. Very short (less than a second) interval image captures can be performed and combined to create a video. Time-lapsed videos over longer interval image captures can also be created. The three-dimensional superimposed image of the first performance can be a first three-dimensional superimposed image and the three-dimensional superimposed image of the second performance can be a second three-dimensional superimposed image. The method can further comprise comparing the first and second three-dimensional superimposed images to determine a wound healing status. The wound progression status can comprise a wound deterioration and the method can further comprise administering at least one wound amelioration aid. The comparison can further comprise tracking a topography of the wound over time. For example, three-dimensional fluorescent imaging can be used to assist with wound debridement for removing bacterial burden. The imaging can be further used to track the results of the debridement over time in three dimensions at a topographical level. Using this approach, a clinician can debride a wound at one visit and track the effect of surgical or curettage debridement over time in three dimensions as well as two dimensions.

Wound healing can be assessed by planimetric measurements of the wound area at multiple time points (for example, at clinical visits) until wound healing. The time course of wound healing can be compared to the expected healing time calculated by the multiple time point measurements of wound radius reduction using the equation $R=\sqrt{A/\pi}$ (R, radius; A, planimetric wound area; $\pi$, constant 3.14). This quantitative information about the wound can be used to track and monitor changes in the wound appearance over time, in order to evaluate and determine the degree of wound healing caused by natural means or by any therapeutic intervention. This data can be stored electronically in the health record of the patient for future reference. Wound imaging can capture, calculate, and/or combine one or more of tissue/bacterial fluorescence, measured wound area, a thermal map of a wound, and an infrared imaging of blood flow.

By changing the excitation and emission wavelengths accordingly, the imaging device can interrogate tissue components (for example, connective tissues and bacteria in a wound) at the surface and at certain depths within the tissue (for example, a wound). For example, by changing from violet/blue (from about 400 nm to about 500 nm) to green (from about 500 nm to about 540 nm) wavelength light, excitation of deeper tissue/bacterial fluorescent sources can be achieved. This can be achieved, for example, in a wound. Similarly, by detecting longer wavelengths, fluorescence emission from tissue and/or bacterial sources deeper in the tissue can be detected at the tissue surface. For wound assessment, the ability to interrogate surface and/or subsurface fluorescence can be useful, for example in detection and potential identification of bacterial contamination, colonization, critical colonization and/or infection, which can occur at the surface and often at depth within a wound (for example, in chronic non-healing wounds). The at least one fluorescent molecule detected by the imaging can comprise a fluorescent molecule associated with at least one bacterium.

The biological target can comprise a tissue excised from a subject organism. For example, the tissue can comprise a precancerous or cancerous tissue. The cancerous tissue can comprise a tumor. For example, the tumor can be a breast tumor and the excised tissue can comprise a lumpectomy. The breast cancer can comprise any type or combination of types of breast cancer. For example, the breast cancer can be a luminal A breast cancer expressing cytokeratins 8 and 18 as well as high levels of estrogen receptor expression. The breast cancer can be a luminal B breast cancer. The breast cancer can be normal breast-like with respect to gene expression. The breast cancer can be HER2 amplified (amplification of the HER2 gene on chromosome 17q). The breast cancer type can be basal type that can be negative for certain receptors (estrogen, progesterone, and HER2) and have markers characteristic of basal/myoepithelial cells. A breast cancer can be characterized by one or more mutations in a BRCA1 gene, a BRCA2 gene, or both.

The cancerous tissue can be a pre-malignant growth, malignant growth, or tumor caused by abnormal and uncontrolled cell division that can be metastatic or non-metastatic. The cancer can be, for example, breast cancer, prostate cancer, lung cancer, colon cancer, rectal cancer, urinary bladder cancer, non-Hodgkin lymphoma, melanoma, renal cancer, pancreatic cancer, cancer of the oral cavity, pharynx cancer, ovarian cancer, thyroid cancer, stomach cancer, brain cancer, multiple myeloma, esophageal cancer, liver cancer, cervical cancer, larynx cancer, cancer of the intrahepatic bile duct, acute myeloid leukemia, soft tissue cancer, small intestine cancer, testicular cancer, chronic lymphocytic leukemia, Hodgkin lymphoma, chronic myeloid cancer, acute lymphocytic cancer, cancer of the anus, anal canal, or anorectum, cancer of the vulva or cancer of the neck, gallbladder, or pleura, malignant mesothelioma, bone cancer, cancer of the joints, hypopharynx cancer, cancer of the eye, cancer of the nose, nasal cavity, neck, or middle ear, nasopharynx cancer, ureter cancer, peritoneum, omentum, or mesentery cancer, or gastrointestinal carcinoid tumor, or any combination thereof. The excised tissue can comprise a fluorescent molecule associated with a probe targeting a tumor receptor, an enzyme-activated fluorescent molecule, or a genetically modified oncolytic virus-induced fluorescence, or any combination thereof. For example, the tumor receptor can comprise HER2, a folate receptor, CXCR4, a hormone receptor, an EGFR, or a VEGF, or a combination thereof. Examples of hormone receptors include estrogen receptors and progesterone receptors. The enzyme can comprise, for example, a protease, a carbohydrase, a lipase, a transferase, an oxidoreductase, a matrix metalloprotease (MMP), a caspase, a cathepsin, a kallikrein, serine protease, isocitrate dehydrogenase, or an enzyme overexpressed by tumor cells, or a combination thereof. The biological target can comprise a surgical bed from which a tissue has been excised. The surgical bed and the excised tissue can comprise a cancerous tissue. The cancerous tissue can be benign, malignant, or both. The tissue removed need not be cancerous and the techniques of the present disclosure can be used in other contexts, for example, plastic surgery, reconstructive surgery, organ transplant surgery, skin grafting, and cosmetic surgery.

The method can be performed any appropriate number of times. For example, the method can be performed at least twice, in either order, the two performances comprising a first performance and a second performance. The first performance can be performed on the biological target. For example, the biological target being a first biological target comprising an excised tissue. The second performance can be performed on a second biological target comprising a surgical bed from which the tissue is excised. The three-dimensional superimposed image of the first performance can be a first three-dimensional superimposed image and the three-dimensional superimposed image of the second performance can be a second three-dimensional superimposed image. The method can further comprise comparing the first and second three-dimensional superimposed images to determine a fluorescent continuity between the excised tissue and the surgical bed based on an orientation of the excised tissue relative to the surgical bed. The fluorescent continuity can comprise, for example, one or more of a bacterially infected tissue, a virally infected tissue, a burn, a cancerous tissue, a connective tissue, a muscle tissue, a blood vesicle, and a skin feature. The fluorescent continuity can correspond to a compromised tissue and the method can further comprise excising at least a portion of the compromised tissue from the surgical bed.

Figure 41:
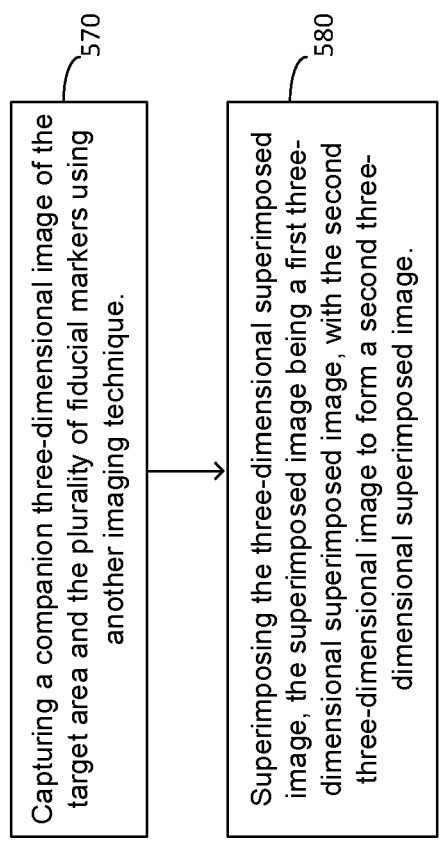
FIG. 41 is a flow chart depicting a method of the present disclosure.

The method can comprise, for example, capturing a companion three-dimensional image of the target area and the one or more fiducial markers using an imaging technique comprising one or more of computerized tomography (CT), magnetic resonance imaging (MRI), photoacoustic imaging, ultrasound, and optical coherence tomography. The three-dimensional superimposed image can be superimposed with the companion three-dimensional image to form a second three-dimensional superimposed image. Examples of such steps designated as 570 and 580 are depicted in FIG. 41. The capturing of the companion three-dimensional image can include first and second sets of fiduciary markers. The companion three-dimensional image can be captured using computerized tomography and the one or more fiducial markers can comprise at least one fluorescent molecule and at least one CT contrast agent. The companion three-dimensional image can be captured using photoacoustic imaging, the target area can comprise a breast tumor, and the at least one fluorescent molecule can comprise an anti-HER2 dual fluorescence-photoacoustic probe.

Any suitable number or type of fiducial marker can be employed. Any suitable number of sets of fiducial markers can be employed. The number of fiducial markers employed can comprise, for example, 1, 2, 3, 4, 5, 6, 7, 8, 9, 10, 12, 15, 20, or 25, or more fiducial markers. The number of sets of fiducial makers employed can be 1, 2, 3, 4, or 5, or more sets. Sets can vary with respect to one or more of placement, size, fluorescence spectrum, fluorescence intensity, and imagining technology specificity of the fiducial markers. Different types of fiducial markers can be colocalized.

The disclosure enables digital integration of pathology data, for example, from histology samples such as those employing a hematoxylin and eosin stain in a three-dimensional data cube of multiple imaging modalities. The data cube permits spatially-localized digital archiving and documenting of location-specific histopathology or other data from the tissue surface of either an ex vivo surgical sample or the surgical bed of a given patient over time. The sites of biopsies can be chronologically catalogued in digital format with corresponding pathology results or other relevant information such as suture site, anastomosis site, implant site, and the like. The cataloging allows a clinical team to tract where tissues have been sampled, the pathology at those sites, and these can be compared before and after a treatment. If tissue deformation occurs in an ex vivo surgical sample, image deformation correction models can be applied to account for the deformation and align with the topographical surface of the surgical bed.

The present disclosure provides a method of spatio-temporally co-registering multimodal imaging two-dimensional and three-dimensional data sets of biological tissues. Further provided are fluorescence and photoacoustic imaging techniques that work in concert with exogenously applied tumor contrast agents to increase the accuracy of detection of tumor cells at surgical margins. The present disclosure provides a clinically useful approach for hybridized surface and volumetric imaging technologies to improve surgical planning, intraoperative guidance, and margin assessment. Otherwise subclinical tumor margins can be identified. Cancer diagnosis can be improved by combining optical imaging data sets, for example, from one or more of photoacoustics, fluorescence, optical coherence tomography (OCT), and Raman imaging including with traditional magnetic resonance imaging (MRI), computer tomography (CT), positron emission tomography (PET), and/or ultrasound (US) scans for tumor diagnosis and response assessment. The ultrasound and other imaging techniques can be two or three dimensional. Doppler imaging (e.g., of blood flow) and/or thermal imaging can also be combined with such other imaging techniques. The disclosed methods, devices, and system also allow for endoscopic imaging and general research.

In accordance with the present disclosure, an imaging device is provided. The imaging device can comprise one or more of the following components. An excitation light source can be configured to emit a first radiation capable of exciting a fluorophore. A filter can be configured to prevent passage of reflected excitation light and permit passage of fluorescence emitted by the fluorophore. An imaging lens can be configured to focus radiation. A visible light source can be configured to emit a second radiation. An infrared light source can be configured to emit a third radiation. At least one image sensor can be configured to detect radiation. A processor can be configured to receive the detected radiation and to output data associated with the detected radiation. The imaging device can be configured to perform one or more of the methods, or portions thereof, described herein. The imaging device can be configured to be hand-held. For example, the imaging device can be configured to be held in one hand.

The imaging device can be configured to visualize any appropriate target area of a biological target, other kind of target, or a combination thereof. The imaging device can be configured to visualize a wound. The imaging device can be configured to visualize one or more of a precancerous cell, a cancerous cell, and a satellite lesion in a surgical margin. The excitation light source can be further configured to excite autofluorescence emissions of tissue cells and fluorescence emissions of induced porphyrins in tissue cells of the surgical margin. The filter can be further configured to prevent passage of reflected excitation light and permit passage of emissions having a wavelength corresponding to the autofluorescence emissions of the tissue cells and the fluorescence emissions of the induced porphyrins in the tissue cells. The image sensor can be further configured to detect the filtered autofluorescence emissions of the tissue cells and the fluorescence emissions of the induced porphyrins in the tissue cells of the surgical margin. The processor can be further configured to receive the detected emissions and to output data regarding the detected filtered autofluorescence emissions of the tissue cells and the fluorescence emissions of the induced porphyrins in the tissue cells of the surgical margin.

The detected radiation can comprise one or more of fluorescence, reflected visible light, and reflected infrared light. The detected radiation can comprise fluorescence, reflected visible light, and reflected infrared light. The first radiation can comprise fluorescence. The second radiation can comprise, for example, white light. The second radiation can comprise monochromatic visible light. The third radiation can comprise infrared radiation, for example, near infrared radiation. The at least one image sensor can be configured to detect radiation comprising one or more of the fluorescence, reflected white light, and reflected infrared light. The at least one sensor can comprise any number and/or type of sensor, for example, at least two sensors. The at least two sensors can comprise a first sensor configured to detect fluorescence and a second detector configured to detect reflected visible light. The at least one sensor can comprise at least three sensors comprising a first sensor configured to detect fluorescence, a second detector configured to detect reflected visible light, and a third sensor configured to detect reflected infrared light.

The at least one sensor can comprise a thermal sensor. A device can combine one or more other sensors described herein for three-dimensional imaging with a thermal sensor. A thermal sensor can be used to provide a thermal map to show areas of high temperature that can correlate with the location of bacteria when looking at wound. Imaging can be combined, for example, with three-dimensional ultrasound images of the wound, including Doppler imaging of blood flow. Thermal mapping can be done separately or in combination with three-dimensional mapping. For example, thermal imaging can be done simultaneously with three-dimensional imaging by coupling a thermal imaging sensor to the three-dimensional imaging device. Then the captured thermal images or video can be superimposed topographically on the visible light/fluorescent light images using one or more fiducials. A camera used for three-dimensional imaging can, for example, capture tissue/bacterial fluorescence, measure wound area, capture a thermal map of wound, and/or image infrared of blood flow.

The imaging device can further comprise a common radiation source configured to operate with or as at least one of the light sources. The at least one light source can comprise a converter to convert source radiation emitted from the common radiation source to the first radiation, the second radiation, or the third radiation, or a combination thereof. The converter can comprise, for example, a filter, a lens, a prism, a diffractor, or a quantum dot, or a combination thereof. The excitation light source can comprise a first converter, the visible light source can comprise a second converter, and the infrared light source can comprise a third converter.

The imaging device can further comprise a display unit. Any display unit can be used, for example, a liquid crystal display (LCD), a light emitting display (LED), an organic light emitting display (OLED), plasma, or cathode ray, or any combination thereof. The display unit can be configured to display the data output by the processor. For example, the data can comprise a three-dimensional image. The display unit can comprise a touchscreen and/or any other type of graphic user interface. A display unit can alternatively or additionally be located in a device other than the imaging device.

The imaging device can be configured to visualize a target area of a biological target. The processor can be configured to generate a three-dimensional map of the target area. The three-dimensional map can be generated from infrared light reflected from the target area. The processor can be configured to capture a two-dimensional visible light image of the target area based on the detected radiation. The processor can be configured to create a three-dimensional visible light image of the target area based on the three-dimensional map and the two-dimensional visible light image. The processor can be configured to capture a two-dimensional fluorescence image of the target area based on the detected radiation. The processor can be configured to create a three-dimensional fluorescence image of the target area based on the three-dimensional map and the two-dimensional fluorescence image. The processor can be configured to align a three-dimensional visible light image of the target area with a three-dimensional fluorescence image of the target area to form a three-dimensional superimposed image of the target area. The alignment can be performed based on co-registration of fiducial markers associated with the target area.

According to one or more embodiments, the imaging device can be configured as follows. The imaging device can be configured to be handheld. The excitation light source can be configured to excite autofluorescence emissions of tissue cells and fluorescence emissions having a wavelength of between about 600 nm and about 660 nm in precancerous cells, cancerous cells, and satellite lesions of a surgical margin after exposure to an imaging or contrast agent. The filter can be configured to permit passage of emissions having a wavelength corresponding to autofluorescence emissions of the tissue cells and fluorescence emissions between about 600 nm and about 660 nm in the tissue cells of the surgical margin. The at least one image sensor can be configured to detect the filtered autofluorescence emissions of the tissue cells and the fluorescence emissions between about 600 nm and about 660 nm in the tissue cells of the surgical margin. The processor can be configured to receive the detected emissions and to output data regarding the detected filtered autofluorescence emissions of the tissue cells and the fluorescence emissions between about 600 nm and about 660 nm in the tissue cells of the surgical margin, and to generate a three-dimensional image of one or more of the precancerous cells, the cancerous cells, and the satellite lesions in the surgical margins.

In accordance with an aspect of the present disclosure, a system for three-dimensional fluorescence-based imaging of a target is provided. The system can comprise one or more of the following components, one or more of the components described for the imaging device, or both. At least one excitation light source can be configured to illuminate a target surface with a field of excitation light during fluorescent imaging. Illumination and/or field can be uniform, partially uniform, or non-uniform. At least one white-light source can be configured to illuminate the target surface during white light imaging. At least one infrared radiation source can be configured to emit infrared radiation toward the target surface. An image sensor can detect fluorescence, reflected radiation, or both. A filter can be configured to permit optical signals responsive to illumination of the target surface with the excitation light and having a wavelength corresponding to one or more of bacterial autofluorescence and tissue autofluorescence to pass through the filter to the image sensor. A processor can be configured to, for example, perform one or more of the following. The processor can receive optical signals responsive to illumination of the target with the infrared light. Based on the received signals responsive to illumination of the target with the infrared light, the processor can generate a three-dimensional map of the target surface. The processor can receive detected optical signals responsive to illumination of the target surface with excitation light and generate a two-dimensional fluorescence image of the target surface. The processor can receive optical signals responsive to white light illumination of the target surface and generate a two-dimensional white light image of the target surface, and the processor can combine the three-dimensional map, the fluorescence image, and the white light image to generate a three-dimensional image of the target surface.

In accordance with an aspect of the present disclosure, a computer program product for use with the imaging device is provided. The computer program product can comprise a non-transitory computer readable medium. The non-transitory computer readable medium can store a computer program code for image processing. The computer program code can be executable by the processor in the imaging device to perform one or more of the methods described herein.

EXAMPLES

Example 1: A Tissue Phantom was Used for Demonstrating the Imaging techniques of the present disclosure. To image the complete surface of a lumptectomy sample, it was scanned under white light using a PrimeSense camera and then rescanned after converting the CCD sensor on the PrimeSense device into a fluorescence camera. By using externally placed fiducial markers on the sample surface, the two imaging scans can be co-registered. Fluorescence was excited using a 405 nm LED array that shone light on tissue surface. The PrimeSense system was fitted with optical filters to generate real time fluorescence images as three-dimensional surface renders of excised tissue (tumor) specimens, specifically breast lumpectomies. PrimeSense detected specific fluorescent signatures from both the autofluorescence of the excised tissue and from fluorescence induced by exogenous contrast agents (ALA-induced porphyrins) although the fluorescence imaging can be modified for any number or type of contrast agent.

Figure 1:
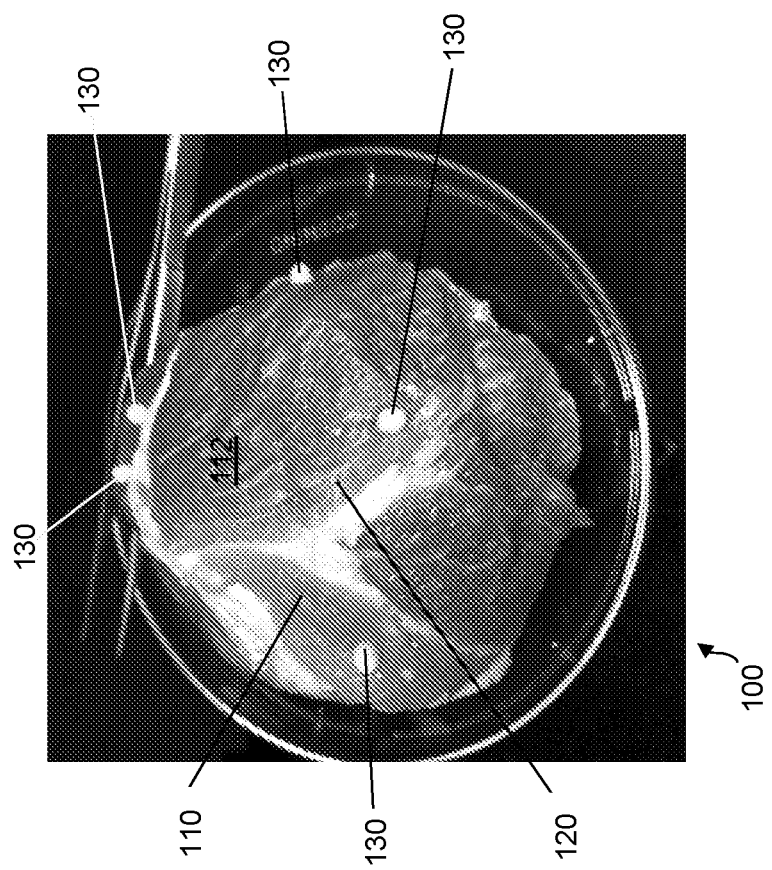
FIG. 1 is a white light photograph of a tissue phantom marked with fluorescein fiducial markers on the surface and with fluorescent PPIX injected just below the surface. The tissue phantom is a piece of pig tissue used to simulate a breast lumpectomy tissue sample.

FIG. 1 is a white light photograph of an experimental model 100 including a tissue phantom 110 marked with fluorescein fiducial markers 130 on a surface 112 of the tissue phantom. The fluorescein fiducial markers can appear yellow/orange under white light and green/yellow under ultraviolet radiation. A simulated tumor 120 is created by fluorescent PPIX injected just below the surface. The fluorescent PPIX generally appears red under ultraviolet radiation. Tissue phantom 110 is a piece of pig tissue used to simulate a breast lumpectomy tissue sample.

Figure 2A:
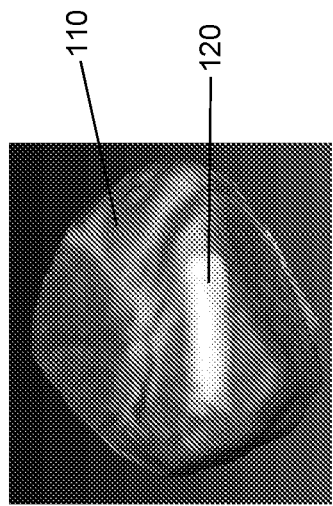
FIG. 2A is a three-dimensional white light surface image of the tissue phantom from a first view angle.
Figure 2B:
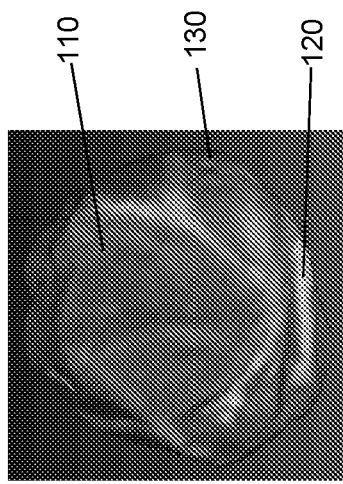
FIG. 2B is a three-dimensional white light surface image of the tissue phantom from a second view angle.
Figure 3A:
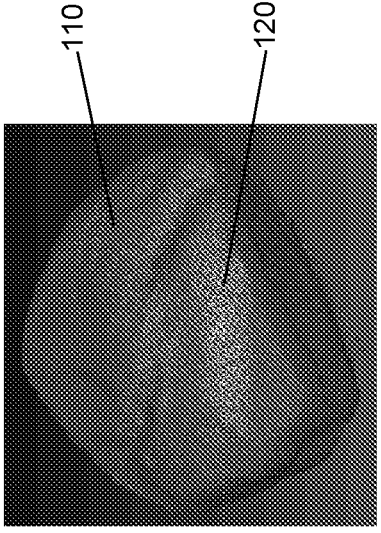
FIG. 3A is a three-dimensional white light surface image of the tissue phantom plus mesh from a first view angle.
Figure 3B:
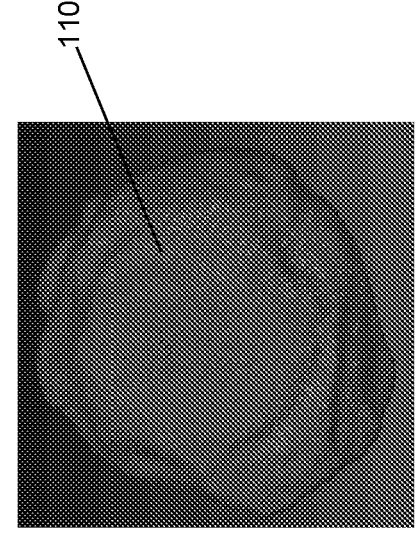
FIG. 3B is a three-dimensional white light surface image of the tissue phantom plus mesh from a second view angle.
Figure 4A:
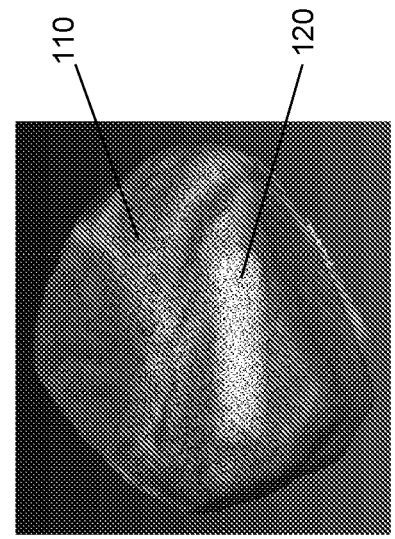
FIG. 4A is a three-dimensional mesh plus white light overlay image of the tissue phantom from a first view angle.
Figure 4B:
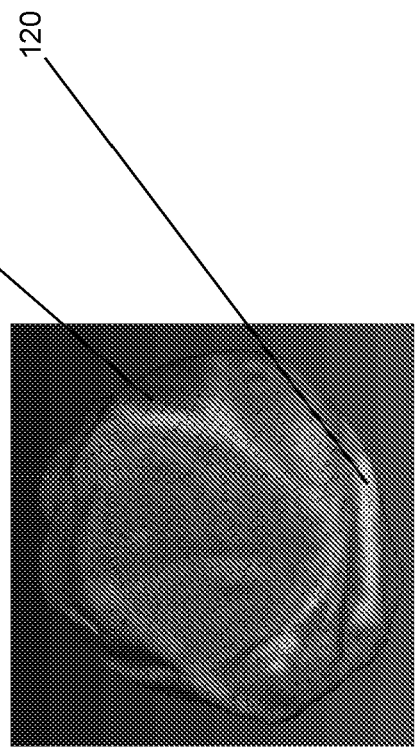
FIG. 4B is a three-dimensional mesh plus white light overlay image of the tissue phantom from a second view angle.
Figure 5A:
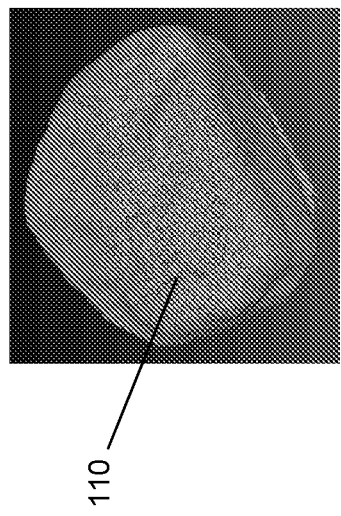
FIG. 5A is a raw mesh/surface image of the tissue phantom from a first view angle.
Figure 5B:
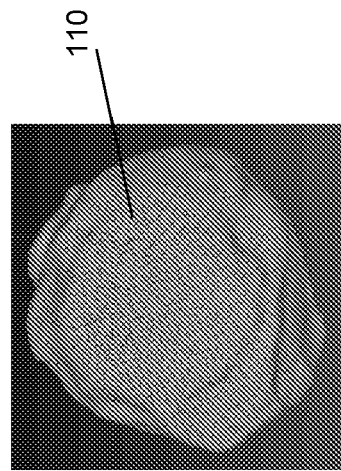
FIG. 5B is a raw mesh/surface image of the tissue phantom from a second view angle.

FIG. 2A is a three-dimensional white light surface image of the tissue phantom 110 from a first view angle. FIG. 2B is a three-dimensional white light surface image of the tissue phantom 110 from a second view angle. FIG. 3A is a three-dimensional white light surface image of the tissue phantom 110 plus mesh from a first view angle. FIG. 3B is a three-dimensional white light surface image of the tissue phantom 110 plus mesh from a second view angle. FIG. 4A is a three-dimensional mesh plus white light overlay image of the tissue phantom 110 from a first view angle. FIG. 4B is a three-dimensional mesh plus white light overlay image of the tissue phantom 110 from a second view angle. FIG. 5A is a raw mesh/surface image of the tissue phantom 110 from a first view angle. FIG. 5B is a raw mesh/surface image of the tissue phantom 110 from a second view angle.

Figure 6A:
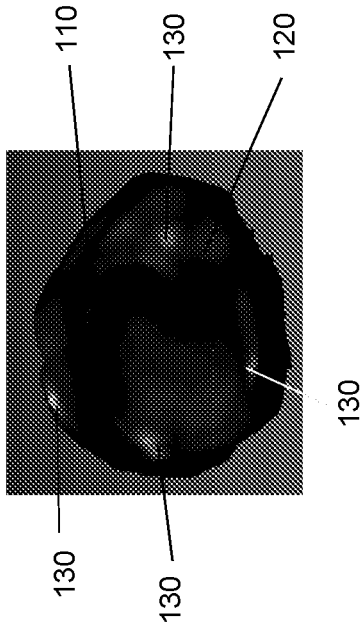
FIG. 6A is a three-dimensional fluorescence surface image of the tissue phantom from a first view angle.
Figure 6B:
FIG. 6B is a three-dimensional fluorescence surface image of the tissue phantom from a second view angle.
Figure 7A:
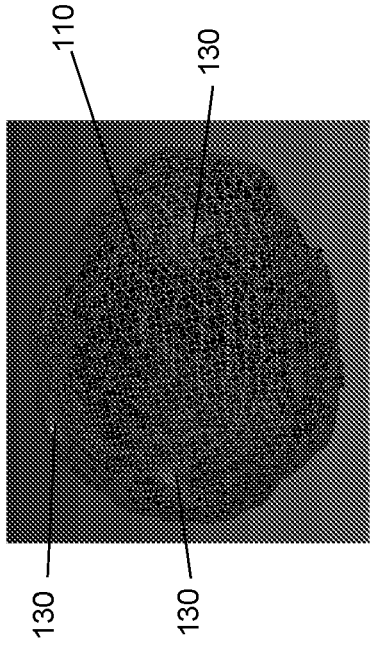
FIG. 7A is a three-dimensional fluorescence surface image of the tissue phantom plus mesh from a first view angle.
Figure 7B:
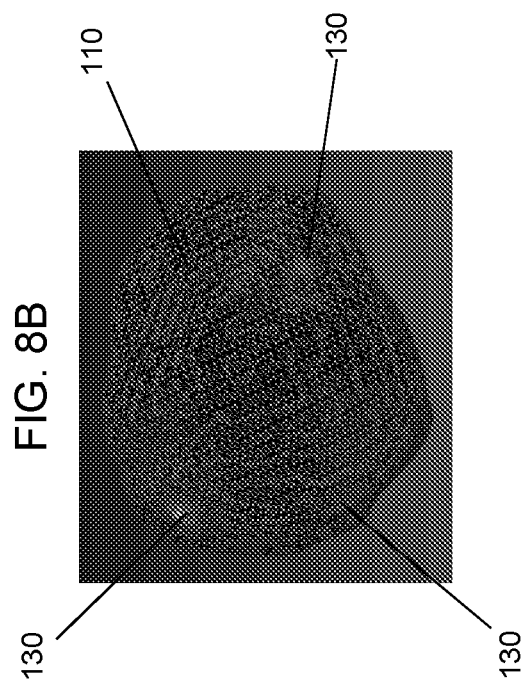
FIG. 7B is a three-dimensional fluorescence surface image of the tissue phantom plus mesh from a second view angle.
Figure 8A:
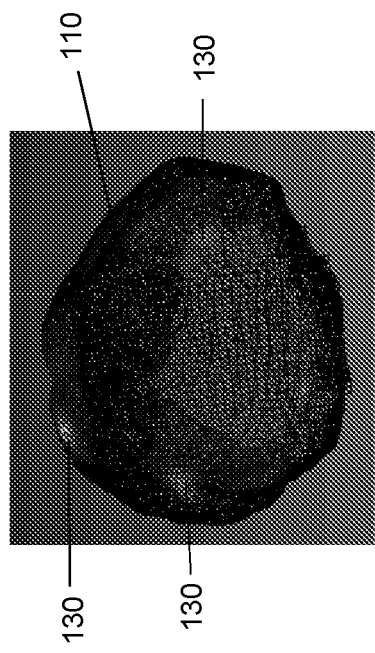
FIG. 8A is a three-dimensional mesh plus fluorescence overlay image of the tissue phantom from a first view angle.
Figure 8B:
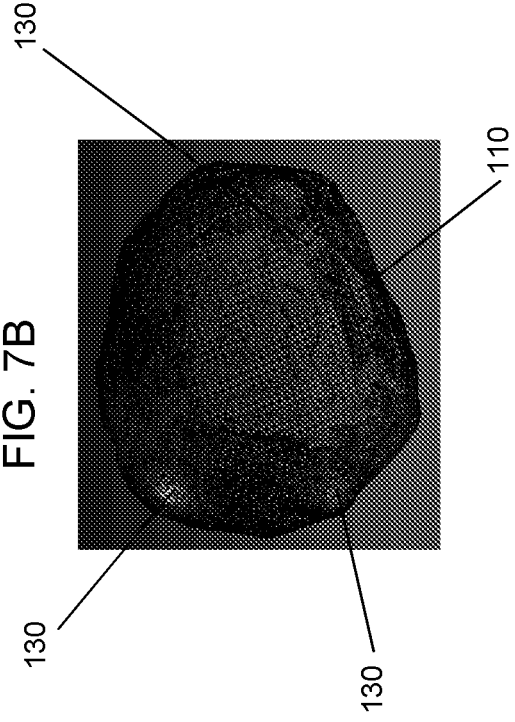
FIG. 8B is a three-dimensional mesh plus fluorescence overlay image of the tissue phantom from a second view angle.
Figure 9A:
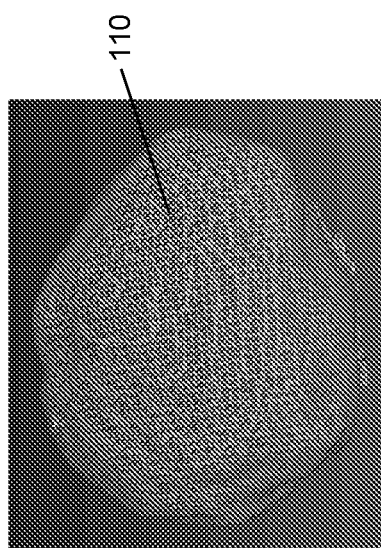
FIG. 9A is a raw mesh/surface image of the tissue phantom from a first view angle.
Figure 9B:
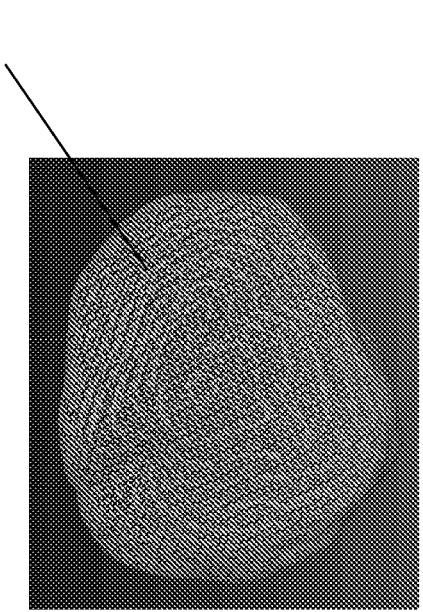
FIG. 9B is a raw mesh/surface image of the tissue phantom from a second view angle.

Red fluorescence in the following figures generally indicates the "tumor" simulated using added PPIX. The simulated tumor graphically represents what a breast lumpectomy would look like with a positive (red fluorescence) margin. FIG. 6A is a three-dimensional fluorescence surface image of the tissue phantom 110 from a first view angle. FIG. 6B is a three-dimensional fluorescence surface image of the tissue phantom 110 from a second view angle. FIG. 7A is a three-dimensional fluorescence surface image of the tissue phantom 110 plus mesh from a first view angle. FIG. 7B is a three-dimensional fluorescence surface image of the tissue phantom 110 plus mesh from a second view angle. FIG. 8A is a three-dimensional mesh plus fluorescence overlay image of the tissue phantom 110 from a first view angle. FIG. 8B is a three-dimensional mesh plus fluorescence overlay image of the tissue phantom 110 from a second view angle. FIG. 9A is a raw mesh/surface image of the tissue phantom 110 from a first view angle. FIG. 9B is a raw mesh/surface image of the tissue phantom 110 from a second view angle.

A multimodal (optical, CT) fiducial marker using mixed fluorescence and CT dyes for co-registration of three-dimensional surface rendered white light reflectance and fluorescence images with three-dimensional surface rendered computer tomography of the phantom was used. The excitation light was 405 nm. The emission filter was a dual band 500-550 nm and 600-650 nm emission filter. This filter was placed within a long plastic filter holder that can slide into and out of position in front of the image sensor of the RGB camera to modify the RGB camera from a white light imaging camera into a fluorescence imaging camera. The camera was connected to a laptop running the PrimeSense data collection software. An external light source was used to illuminate the target area of the biological target (a pig leg with a skin wound) with 405 nm light from two LEDs. Cone beam CT scan image processing utilized InVesalius 3 software.

Figure 10A:
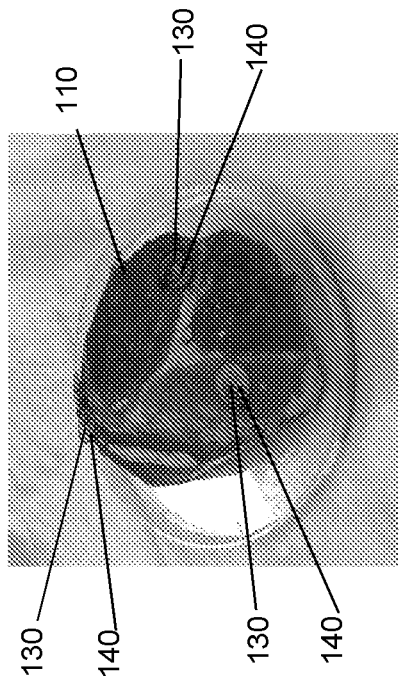
FIG. 10A is a first view of the tissue phantom having CT fiducials overlaid on fluorescent fiducials.
Figure 10B:
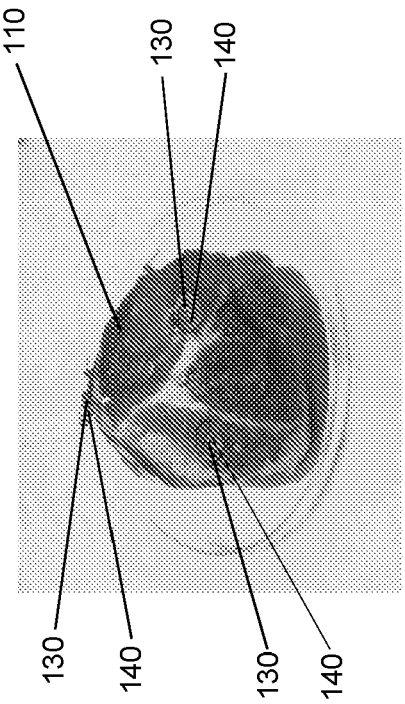
FIG. 10B is a second view of the tissue phantom having CT fiducials overlaid on fluorescent fiducials.
Figure 11C:
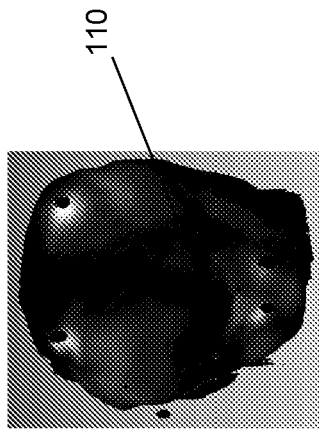
FIG. 11C is a co-registered CT plus fluorescence image of the tissue phantom from a first view angle.
Figure 12C:
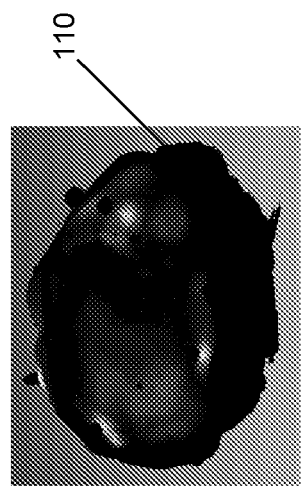
FIG. 12C is a co-registered CT plus fluorescence image of the tissue phantom from a second view angle.
Figure 11B:
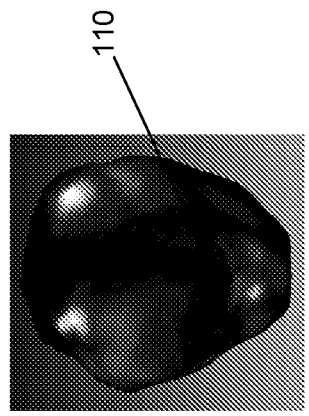
FIG. 11B is a fluorescence three-dimensional render of the tissue phantom from a first view angle.
Figure 12B:
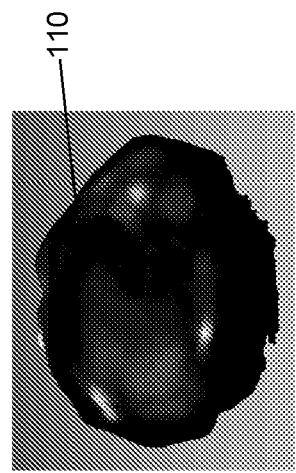
FIG. 12B is a fluorescence three-dimensional render of the tissue phantom from a second view angle.
Figure 11A:
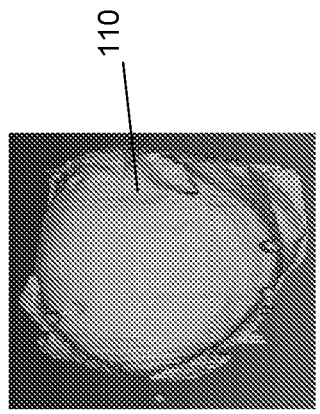
FIG. 11A is a cone beam CT three-dimensional volume reconstruction of the tissue phantom from a first view angle.
Figure 12A:
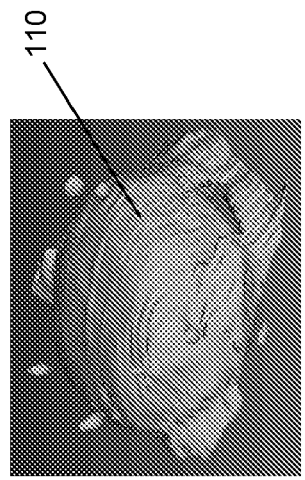
FIG. 12A is a cone beam CT three-dimensional volume reconstruction of the tissue phantom from a second view angle.
Figure 13A:
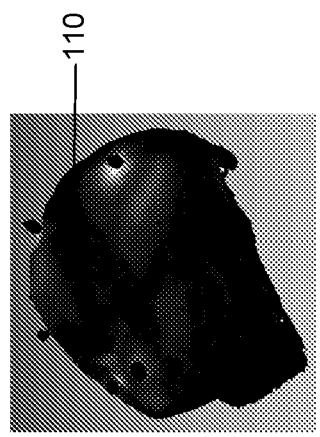
FIG. 13A is a cone beam CT three-dimensional volume reconstruction of the tissue phantom from a third view angle.
Figure 13B:
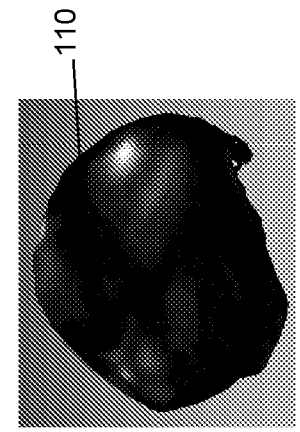
FIG. 13B is a fluorescence three-dimensional render of the tissue phantom from a first view angle.
Figure 13C:
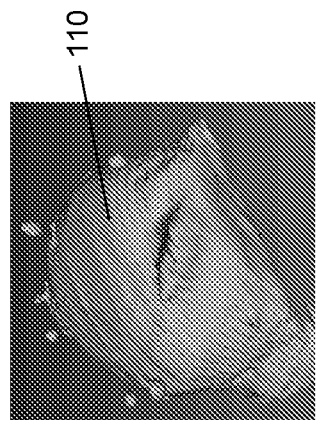
FIG. 13C is a co-registered CT plus fluorescence image of the tissue phantom from a third view angle.
Figure 14A:
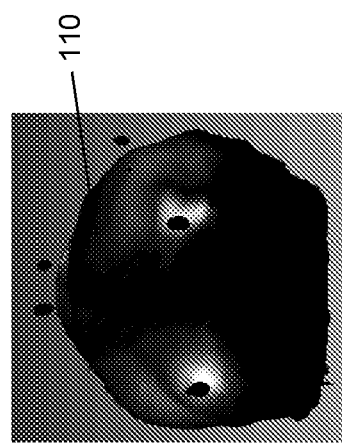
FIG. 14A is a cone beam CT three-dimensional volume reconstruction of the tissue phantom from a fourth view angle.
Figure 14B:
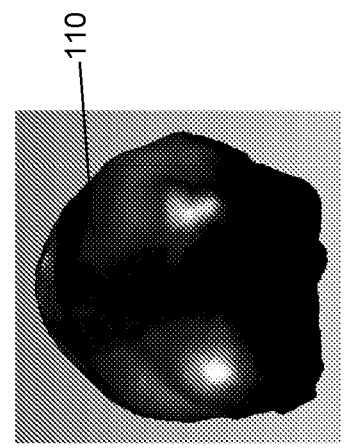
FIG. 14B is a fluorescence three-dimensional render of the tissue phantom from a fourth view angle.
Figure 14C:
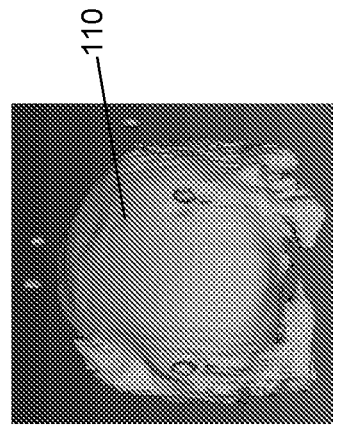
FIG. 14C is a co-registered CT plus fluorescence image of the tissue phantom from a fourth view angle.

FIG. 10A is a first view of the tissue phantom 110 having CT fiducials 140 overlaid on fluorescent fiducials 130. FIG. 10B is a second view of the tissue phantom having CT fiducials overlaid on fluorescent fiducials. Red fluorescence in the following figures generally indicates the "tumor" simulated using added PPIX. The simulated tumor graphically represents what a breast lumpectomy would look like with a positive (red fluorescence) margin. FIG. 11A is a cone beam CT three-dimensional volume reconstruction of the tissue phantom 110 from a first view angle. FIG. 11B is a fluorescence three-dimensional render of the tissue phantom 110 from a first view angle. FIG. 11C is a co-registered CT plus fluorescence image of the tissue phantom 110 from a first view angle. FIG. 12A is a cone beam CT three-dimensional volume reconstruction of the tissue phantom 110 from a second view angle. FIG. 12B is a fluorescence three-dimensional render of the tissue phantom 110 from a second view angle. FIG. 12C is a co-registered CT plus fluorescence image of the tissue phantom 110 from a second view angle. FIG. 13A is a cone beam CT three-dimensional volume reconstruction of the tissue phantom 110 from a third view angle. FIG. 13B is a fluorescence three-dimensional render of the tissue phantom 110 from a first view angle. FIG. 13C is a co-registered CT plus fluorescence image of the tissue phantom 110 from a third view angle. FIG. 14A is a cone beam CT three-dimensional volume reconstruction of the tissue phantom 110 from a fourth view angle. FIG. 14B is a fluorescence three-dimensional render of the tissue phantom 110 from a fourth view angle. FIG. 14C is a co-registered CT plus fluorescence image of the tissue phantom 110 from a fourth view angle.

These figures show the ability of the techniques of the present disclosure to create three-dimensional images of tissues and other objects that serve as valuable tools for better characterizing and understanding the tissues and other objects. A surgeon, for example, can be better visualize the extent of cancerous tissue in a patient and formulate excisions to efficiently remove the cancerous tissue while sparing adjacent healthy tissue. Thus, Example 1 demonstrates the effectiveness of the disclosed techniques.

Example 2

Figure 15B:
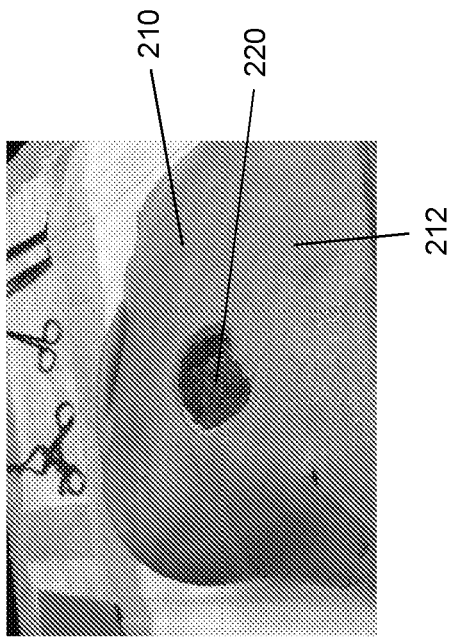
FIG. 15B is a second image of a second tissue phantom for a tumor model during preparation.
Figure 15A:
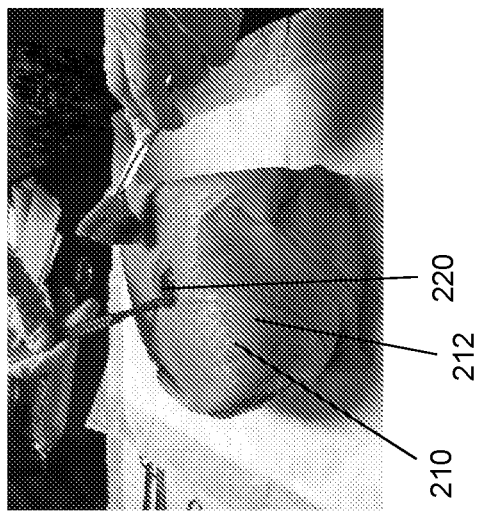
FIG. 15A is a first image of a second tissue phantom for a tumor model during preparation from a pig shoulder that has skin similar to human skin.
Figure 16:
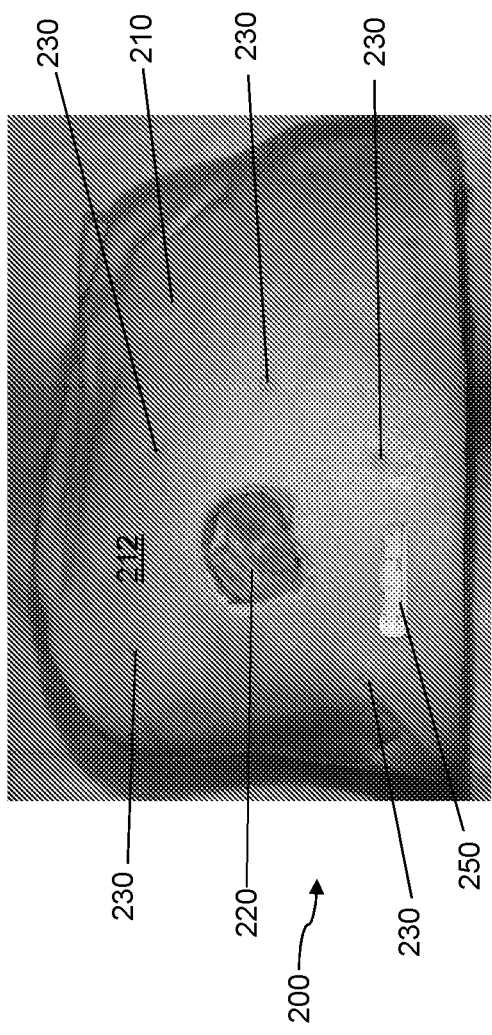
FIG. 16 is an image of the second tissue phantom showing the model PPIX tumor and fluorescein fiducial markers are also visible.
Figure 17B:
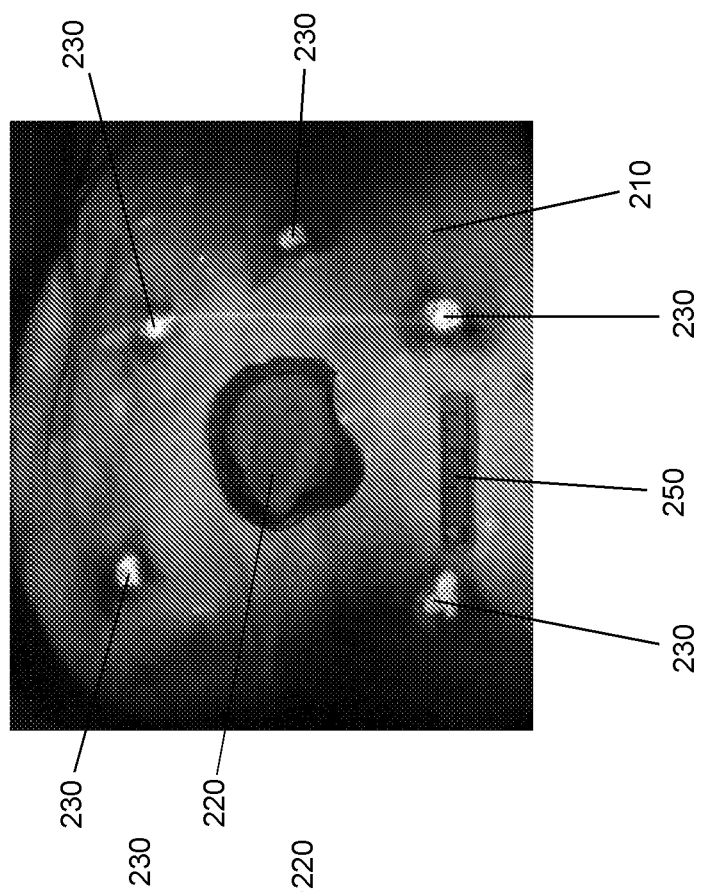
FIG. 17B is an image of a plan view of an emission image of the second tissue phantom exposed to violet light to excite fluorescence.
Figure 17A:
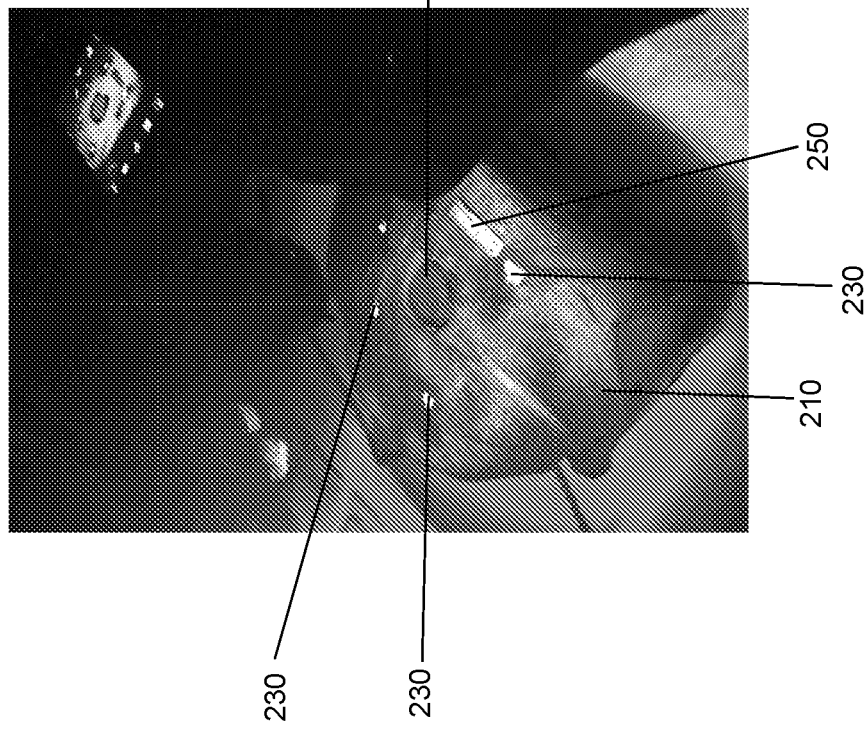
FIG. 17A is an image of a perspective view of the second tissue phantom exposed to violet light to excite fluorescence.
Figure 18A:
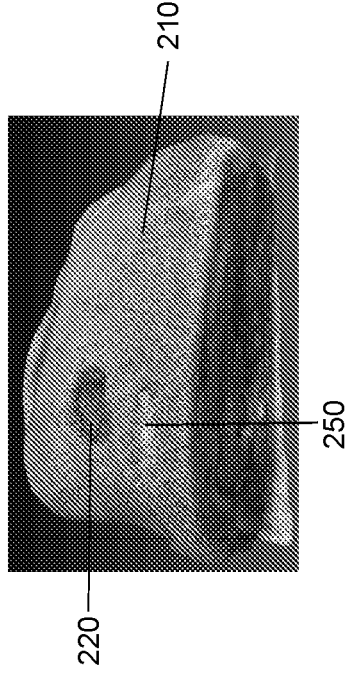
FIG. 18A is a three-dimensional white light surface image of the second tissue phantom from a first view angle.
Figure 18B:
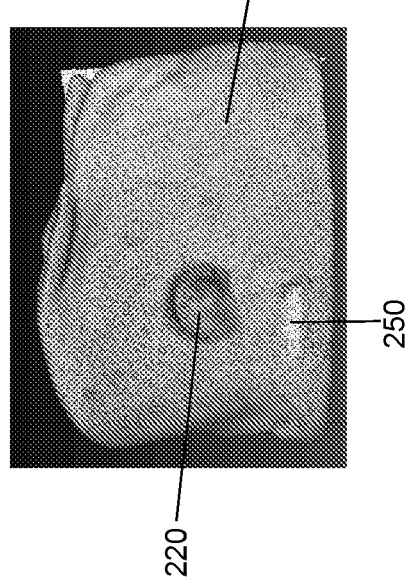
FIG. 18B is a three-dimensional white light surface image of the second tissue phantom from a second view angle.
Figure 19A:
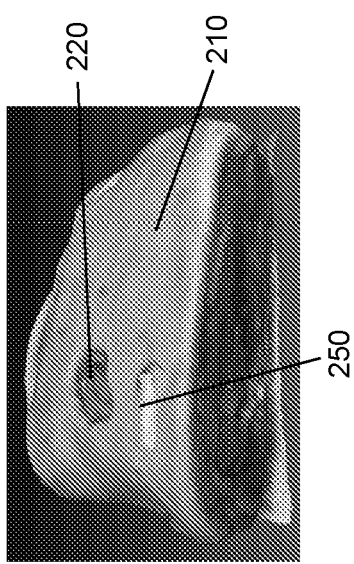
FIG. 19A is a three-dimensional white light surface image of the second tissue phantom plus mesh from a first view angle.
Figure 19B:
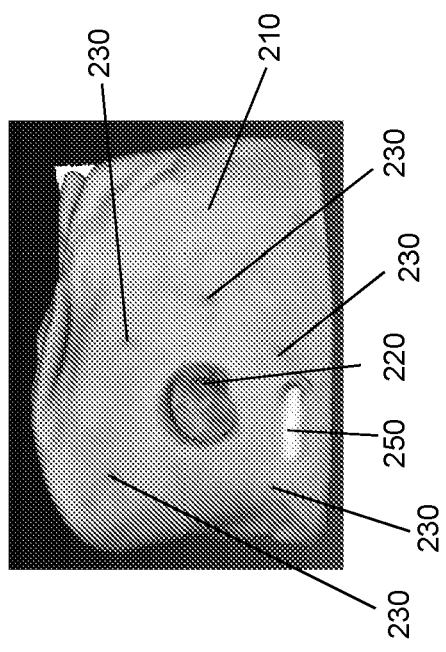
FIG. 19B is a three-dimensional white light surface image of the second tissue phantom plus mesh from a second view angle.
Figure 21A:
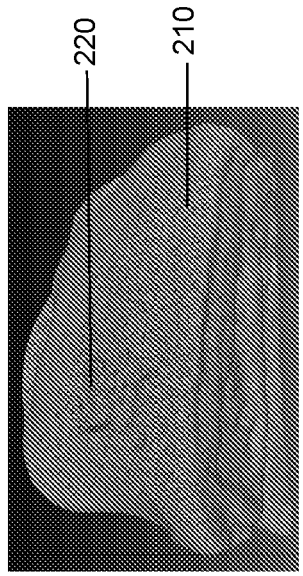
FIG. 21A is a raw mesh/surface image of the second tissue phantom from a first view angle.
Figure 21B:
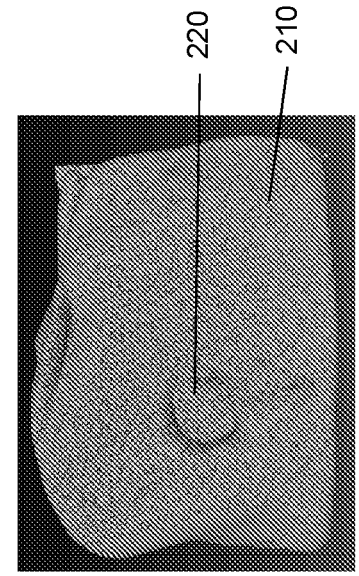
FIG. 21B is a raw mesh/surface image of the second tissue phantom from a second view angle.
Figure 20A:
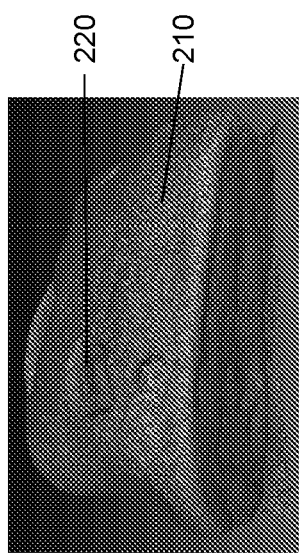
FIG. 20A is a three-dimensional mesh plus white light overlay image of the second tissue phantom from a first view angle.
Figure 20B:
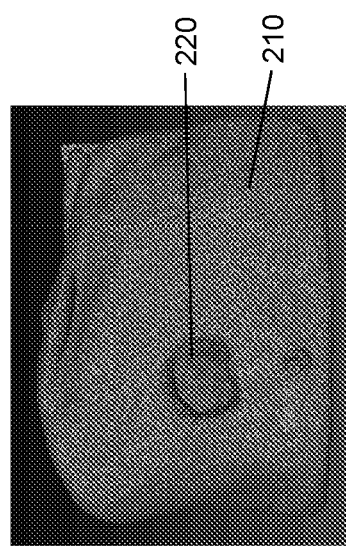
FIG. 20B is a three-dimensional mesh plus white light overlay image of the second tissue phantom from a second view angle.

In this example, procedures were performed essentially the same as in Example 1, but a second experimental model 200 including a second tissue phantom modeling a simulated tumor was used. FIG. 15A is a first image of second tissue phantom 210 for a simulated tumor 220 during preparation from a pig shoulder that has skin (surface) 212 similar to human skin. FIG. 15B is a second image of a second tissue phantom for a tumor model during preparation. FIG. 16 is an image of second tissue phantom 210 showing the simulated (model PPIX) tumor 220 and fluorescein fiducial markers 230 are also visible. A ruler 250 can be used to establish scale. FIG. 17A is an image of a perspective view of the second tissue phantom 210 being exposed to violet light via a handheld imaging device to excite fluorescence. FIG. 17B is an image of a plan view of an image of fluorescence emission from second tissue phantom 210 exposed to violet light to excite fluorescence. FIG. 18A is a three-dimensional white light surface image of the second tissue phantom 210 from a first view angle. FIG. 18B is a three-dimensional white light surface image of the second tissue phantom 210 from a second view angle. FIG. 19A is a three-dimensional white light surface image of the second tissue phantom 210 plus mesh from a first view angle. FIG. 19B is a three-dimensional white light surface image of the second tissue phantom 210 plus mesh from a second view angle. FIG. 20A is a three-dimensional mesh plus white light overlay image of the second tissue phantom 210 from a first view angle. FIG. 20B is a three-dimensional mesh plus white light overlay image of the second tissue phantom 210 from a second view angle. FIG. 21A is a raw mesh/surface image of the second tissue phantom 210 from a first view angle. FIG. 21B is a raw mesh/surface image of the second tissue phantom 210 from a second view angle.

Figure 22A:
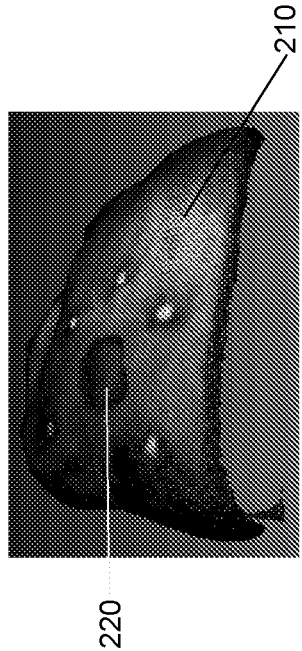
FIG. 22A is a three-dimensional fluorescence surface image of the second tissue phantom from a first view angle.
Figure 23A:
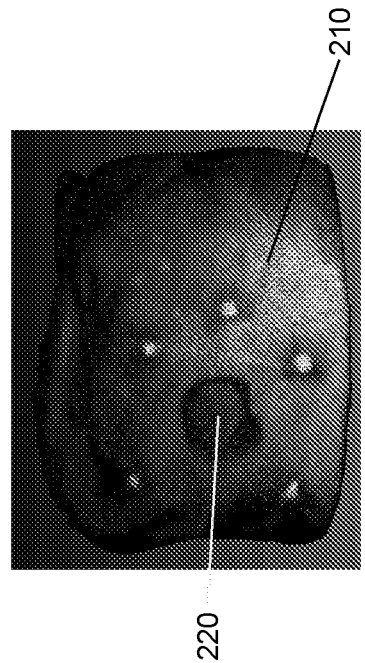
FIG. 23A is a three-dimensional fluorescence surface image of the second tissue phantom plus mesh from a first view angle.
Figure 22B:
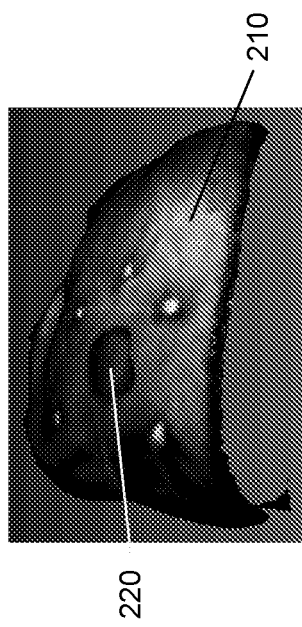
FIG. 22B is a three-dimensional fluorescence surface image of the second tissue phantom from a second view angle.
Figure 23B:
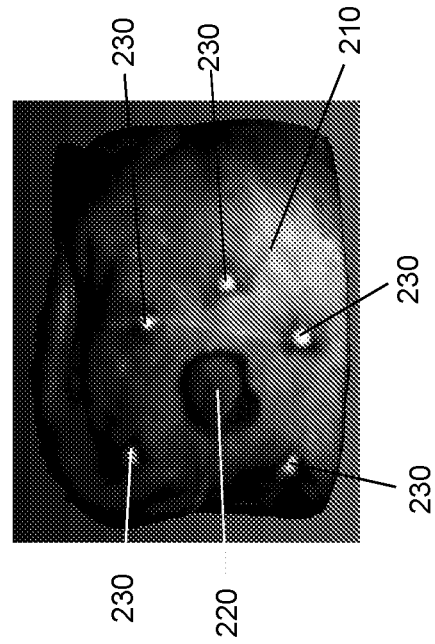
FIG. 23B is a three-dimensional fluorescence surface image of the second tissue phantom plus mesh from a second view angle.
Figure 25A:
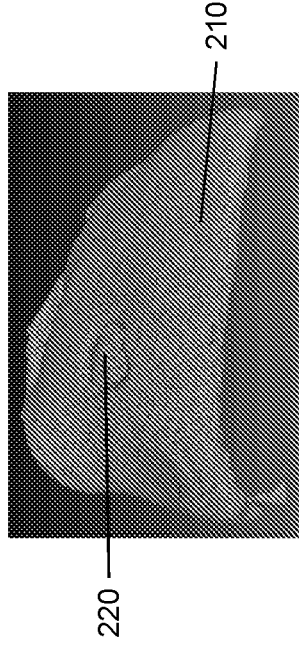
FIG. 25A is a raw mesh/surface image of the second tissue phantom from a first view angle.
Figure 25B:
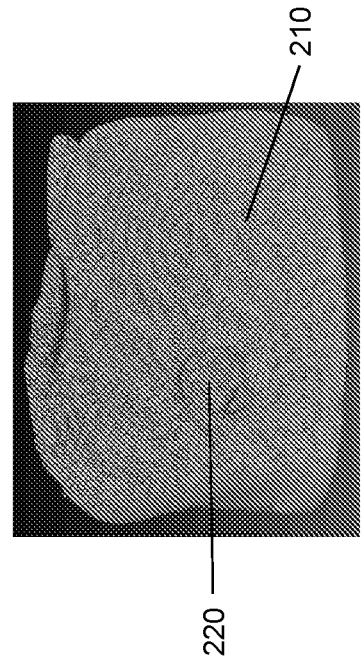
FIG. 25B is a raw mesh/surface image of the second tissue phantom from a second view angle.
Figure 24A:
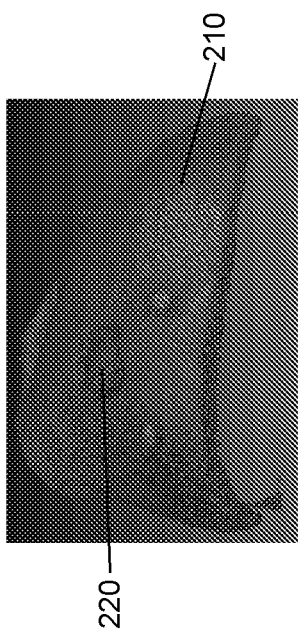
FIG. 24A is a three-dimensional mesh plus fluorescence overlay image of the second tissue phantom from a first view angle.
Figure 24B:
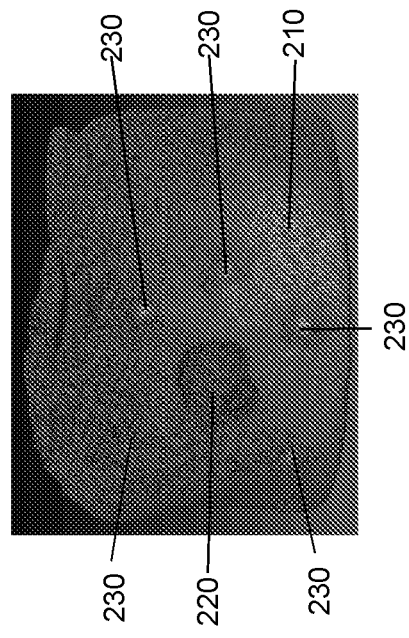
FIG. 24B is a three-dimensional mesh plus fluorescence overlay image of the second tissue phantom from a second view angle.

Red fluorescence in the figures generally indicates the "bacteria" in the periphery of a "wound" simulated using added PPIX. The simulated wounds graphically represent what bacterially infected concave wounds would look like with a positive (red fluorescence) margin. FIG. 22A is a three-dimensional fluorescence surface image of the second tissue phantom 210 from a first view angle. FIG. 22B is a three-dimensional fluorescence surface image of the second tissue phantom 210 from a second view angle. FIG. 23A is a three-dimensional fluorescence surface image of the second tissue phantom 210 plus mesh from a first view angle. FIG. 23B is a three-dimensional fluorescence surface image of the second tissue phantom 210 plus mesh from a second view angle. FIG. 24A is a three-dimensional mesh plus fluorescence overlay image of the second tissue phantom 210 from a first view angle. FIG. 24B is a three-dimensional mesh plus fluorescence overlay image of the second tissue phantom 210 from a second view angle. FIG. 25A is a raw mesh/surface image of the second tissue phantom 210 from a first view angle. FIG. 25B is a raw mesh/surface image of the second tissue phantom 210 from a second view angle.

These figures show the ability of the techniques of the present disclosure to create three-dimensional images of tissues and other objects that serve as valuable tools for better characterizing and understanding the tissues and other objects. A surgeon, for example, can be better visualize the extent of cancerous tissue in a patient and formulate excisions to efficiently remove the cancerous tissue while sparing adjacent healthy tissue. Thus, Example 2 demonstrates the effectiveness of the disclosed techniques.

Example 3

Figure 26B:
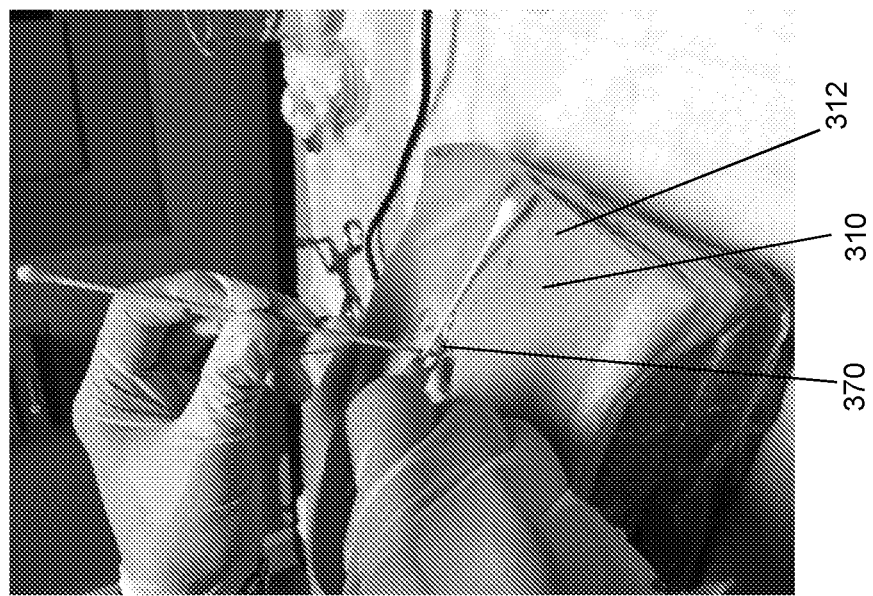
FIG. 26B is a second image of a third tissue phantom for a wound model during preparation.
Figure 26A:
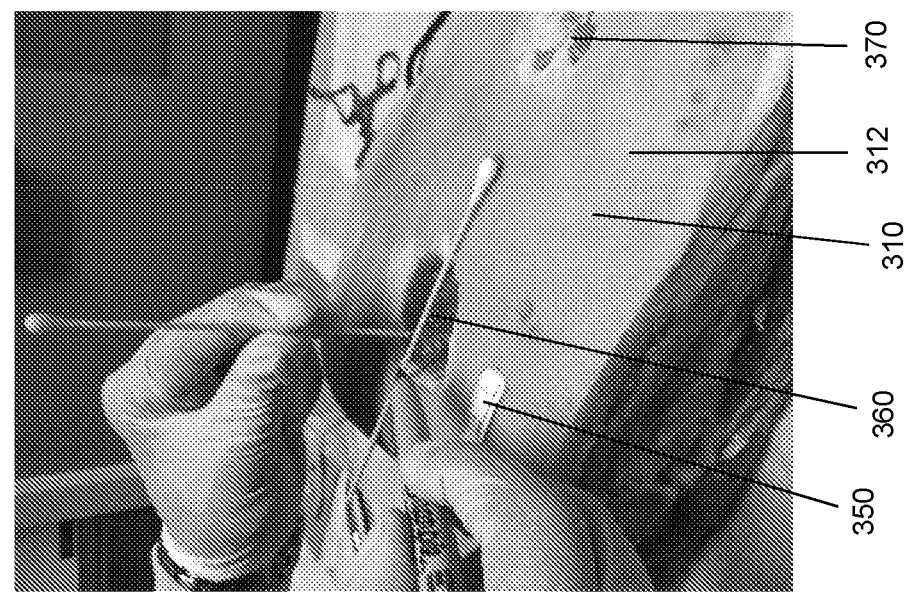
FIG. 26A is a first image of a third tissue phantom for a wound model during preparation.
Figure 26D:
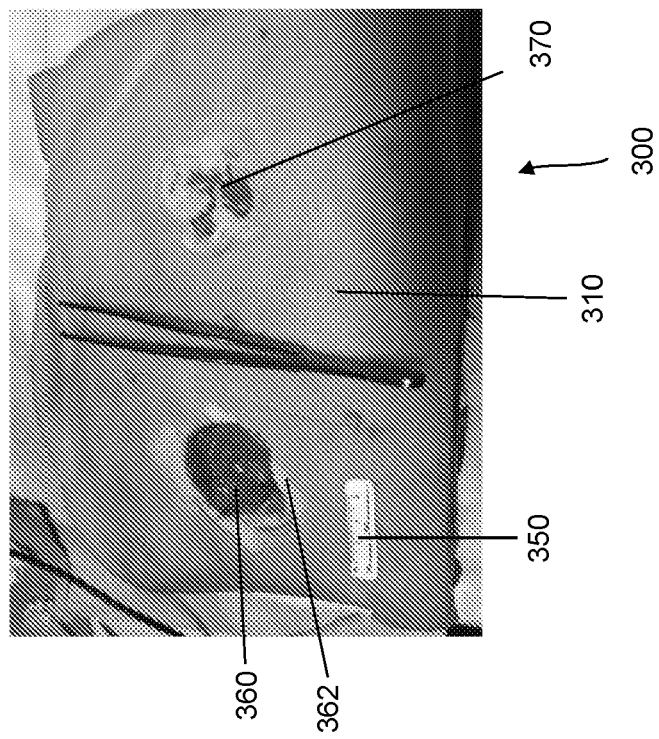
FIG. 26D is a fourth image of a third tissue phantom for a wound model during preparation depicting both a deep wound and a superficial wound, as well as fluorescein fiducial markers.
Figure 26C:
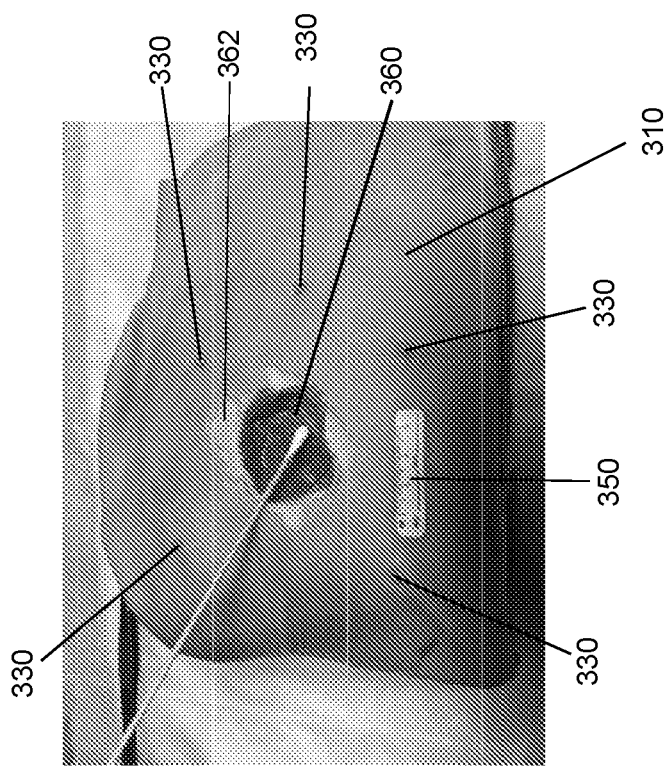
FIG. 26C is a third image of a third tissue phantom for a wound model during preparation depicting a deep wound painted with PPIX to simulate the presence of bacteria in the wound.
Figure 28A:
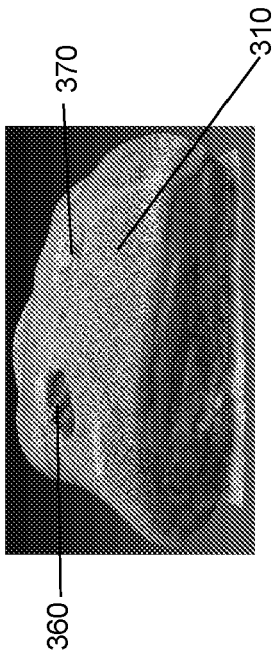
FIG. 28A is a three-dimensional white light surface image of the third tissue phantom plus mesh from a first view angle.
Figure 28B:
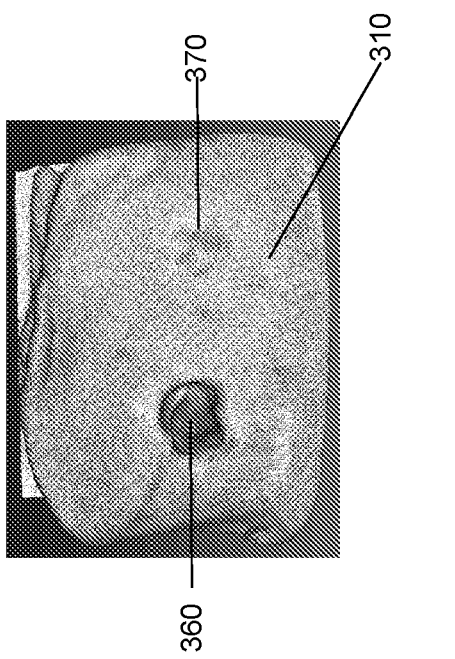
FIG. 28B is a three-dimensional white light surface image of the third tissue phantom plus mesh from a second view angle.
Figure 27A:
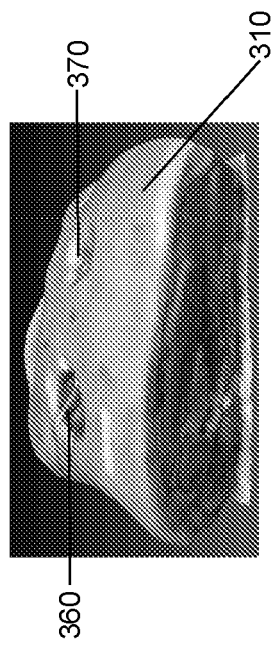
FIG. 27A is a three-dimensional white light surface image of the third tissue phantom from a first view angle.
Figure 27B:
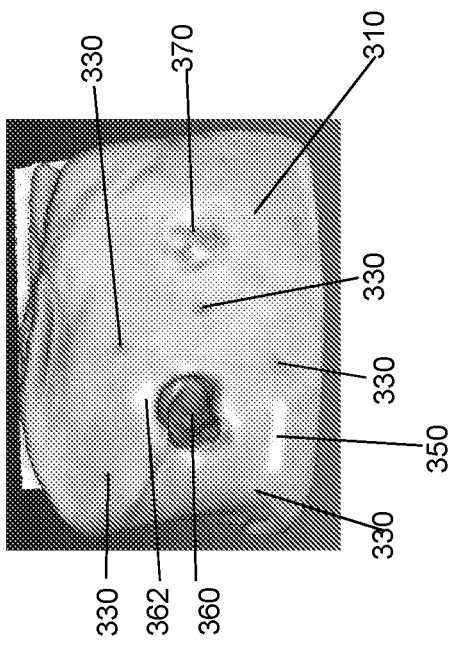
FIG. 27B is a three-dimensional white light surface image of the third tissue phantom from a second view angle.
Figure 29A:
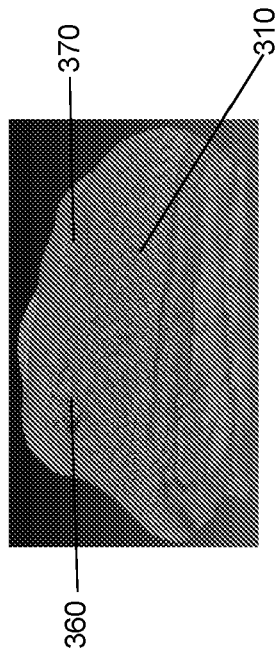
FIG. 29A is a three-dimensional mesh plus white light overlay image of the third tissue phantom from a first view angle.
Figure 29B:
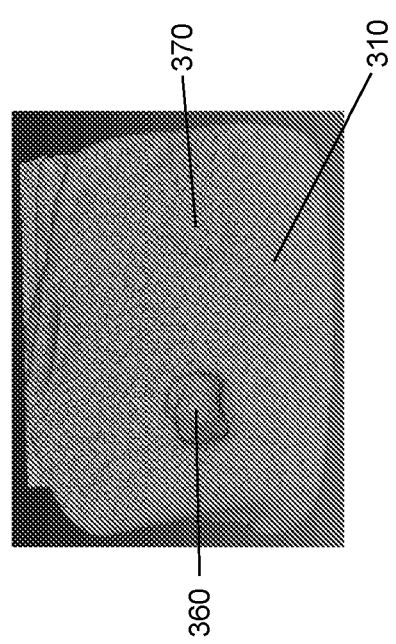
FIG. 29B is a three-dimensional mesh plus white light overlay image of the third tissue phantom from a second view angle.
Figure 30A:
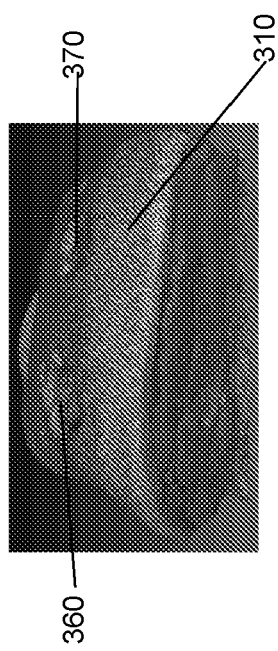
FIG. 30A is a raw mesh/surface image of the third tissue phantom from a first view angle.
Figure 30B:
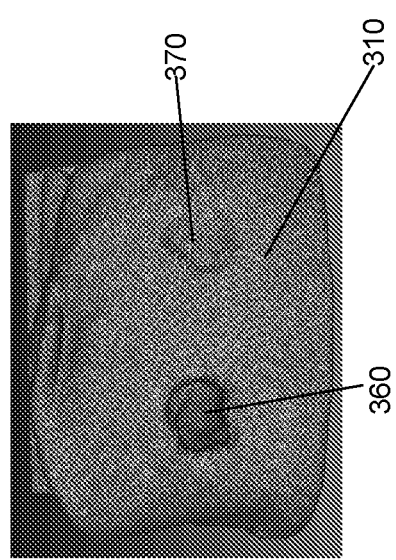
FIG. 30B is a raw mesh/surface image of the third tissue phantom from a second view angle.
Figure 32A:
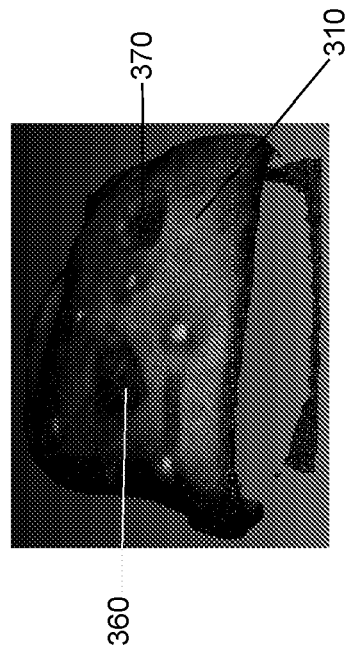
FIG. 32A is a three-dimensional fluorescence surface image of the third tissue phantom plus mesh from a first view angle.
Figure 32B:
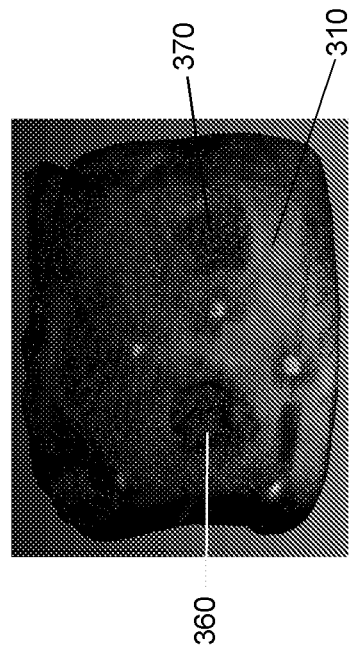
FIG. 32B is a three-dimensional fluorescence surface image of the third tissue phantom plus mesh from a second view angle.
Figure 31A:
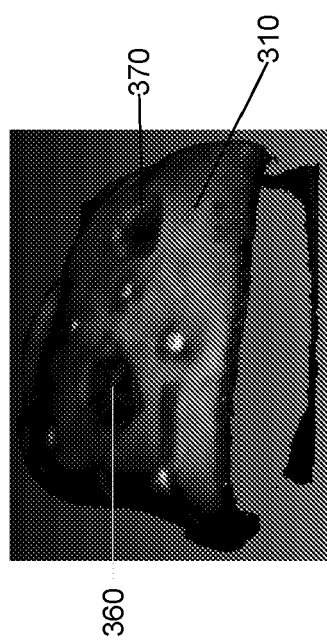
FIG. 31A is a three-dimensional fluorescence surface image of the third tissue phantom from a first view angle.
Figure 31B:
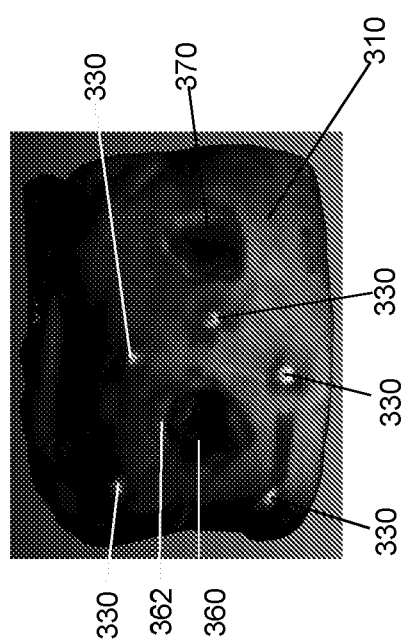
FIG. 31B is a three-dimensional fluorescence surface image of the third tissue phantom from a second view angle.
Figure 33A:
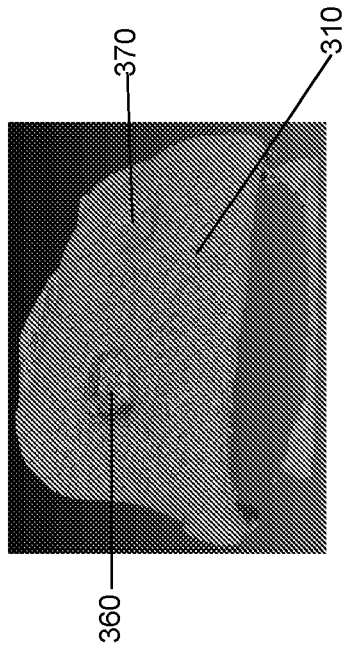
FIG. 33A is a three-dimensional mesh plus fluorescence overlay image of the third tissue phantom from a first view angle.
Figure 33B:
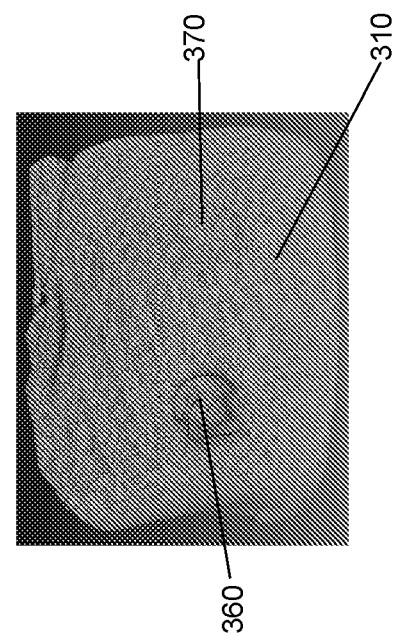
FIG. 33B is a three-dimensional mesh plus fluorescence overlay image of the third tissue phantom from a second view angle.
Figure 34A:
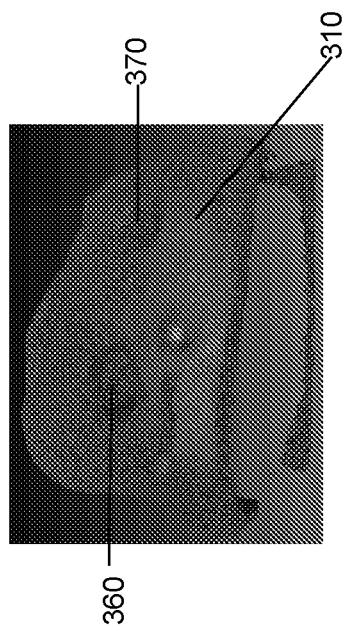
FIG. 34A is a raw mesh/surface image of the third tissue phantom from a first view angle.
Figure 34B:
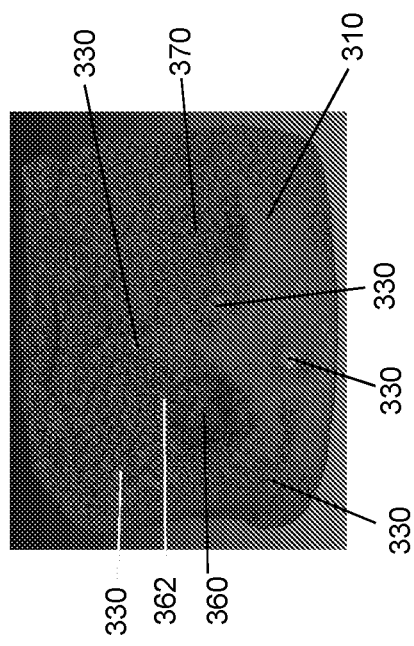
FIG. 34B is a raw mesh/surface image of the third tissue phantom from a second view angle.

In this example, procedures were performed essentially the same as in Example 1, but a third tissue phantom modeling a deep wound and superficial wound was used. Cone beam CT and CT scan image processing utilized InVesalius 3 software. FIG. 26A is a first image of a third tissue phantom 310 for a wound model 300 during preparation on the skin 312 to include both a deep wound 360 and a superficial wound 370. A ruler 350 can be included for scale. FIG. 26B is a second image of a third tissue phantom 310 during preparation. FIG. 26C is a third image of a third tissue phantom 310 during preparation depicting a deep wound 360 including wound periphery 362 painted with PPIX to simulate the presence of bacteria in the wound. FIG. 26D is a fourth image of a third tissue phantom 310 during preparation depicting both a deep wound 360 and a superficial wound 370, as well as fluorescein fiducial markers 330. FIG. 27A is a three-dimensional white light surface image of the third tissue phantom 310 from a first view angle. FIG. 27B is a three-dimensional white light surface image of the third tissue phantom 310 from a second view angle. FIG. 28A is a three-dimensional white light surface image of the third tissue phantom 310 plus mesh from a first view angle. FIG. 28B is a three-dimensional white light surface image of the third tissue phantom 310 plus mesh from a second view angle. FIG. 29A is a three-dimensional mesh plus white light overlay image of the third tissue phantom 310 from a first view angle. FIG. 29B is a three-dimensional mesh plus white light overlay image of the third tissue phantom 310 from a second view angle. FIG. 30A is a raw mesh/surface image of the third tissue phantom 310 from a first view angle. FIG. 30B is a raw mesh/surface image of the third tissue phantom 310 from a second view angle. FIG. 31A is a three-dimensional fluorescence surface image of the third tissue phantom 310 from a first view angle. FIG. 31B is a three-dimensional fluorescence surface image of the third tissue phantom 310 from a second view angle. FIG. 32A is a three-dimensional fluorescence surface image of the third tissue phantom 310 plus mesh from a first view angle. FIG. 32B is a three-dimensional fluorescence surface image of the third tissue phantom 310 plus mesh from a second view angle. FIG. 33A is a three-dimensional mesh plus fluorescence overlay image of the third tissue phantom 310 from a first view angle. FIG. 33B is a three-dimensional mesh plus fluorescence overlay image of the third tissue phantom 310 from a second view angle. FIG. 34A is a raw mesh/surface image of the third tissue phantom 310 from a first view angle. FIG. 34B is a raw mesh/surface image of the third tissue phantom 310 from a second view angle.

Figure 35B:
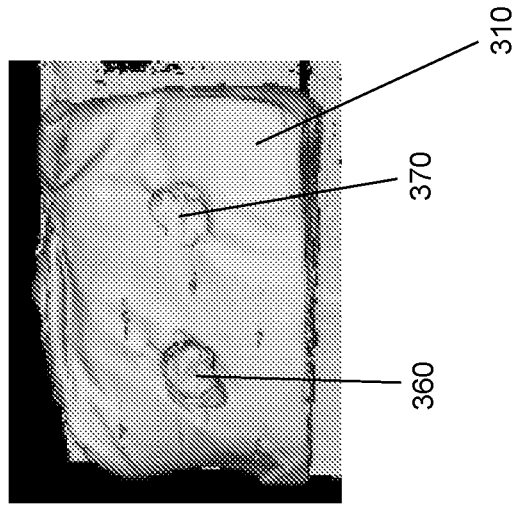
FIG. 35B is a cone beam CT scan image of the third tissue phantom.
Figure 35A:
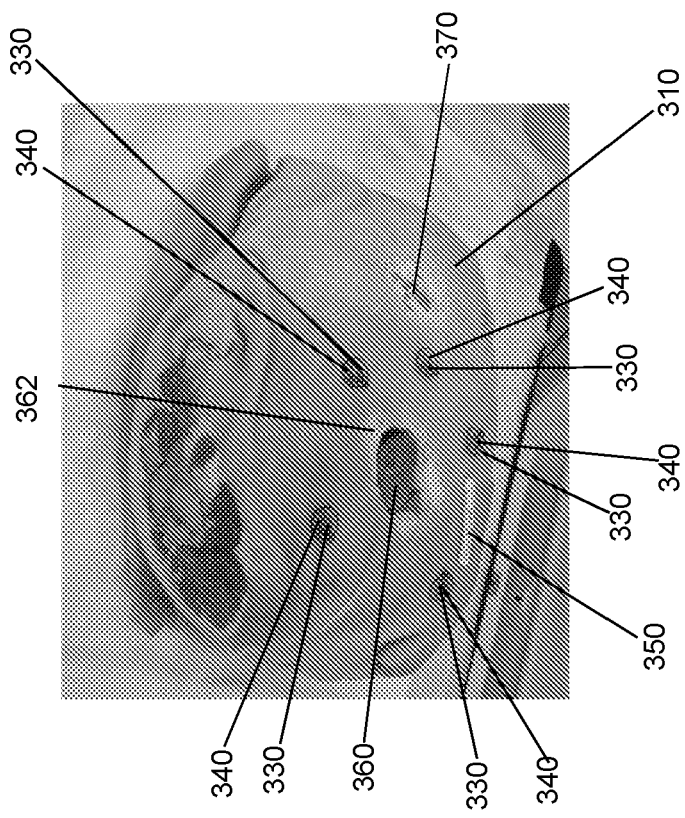
FIG. 35A is an image of the third tissue phantom prepared with CT fiducial markers for a cone beam CT scan.
Figure 36A:
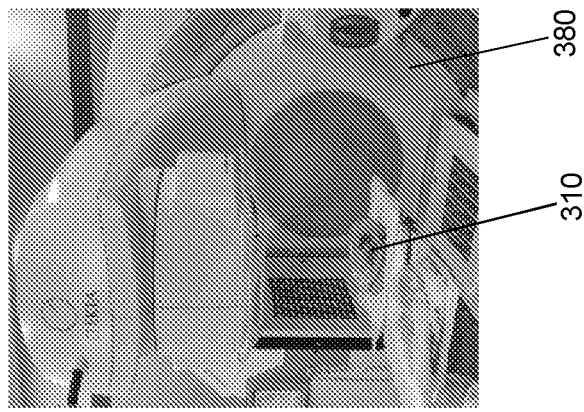
FIG. 36A is an image of the third tissue phantom prepared with CT fiducials spatially co-registered with fluorescein fiducials for a CT scan.
Figure 35D:
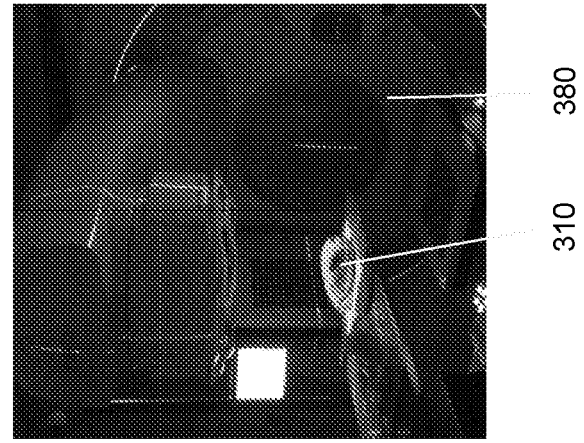
FIG. 35D is an image of the third tissue phantom undergoing a cone beam CT scan.
Figure 35C:
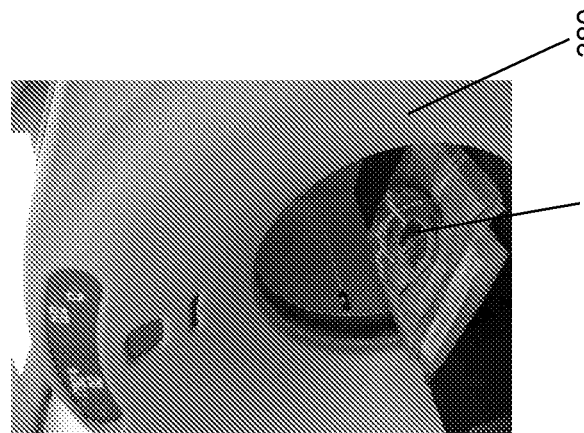
FIG. 35C is an image of the third tissue phantom prepared for a cone beam CT scan.
Figure 37:
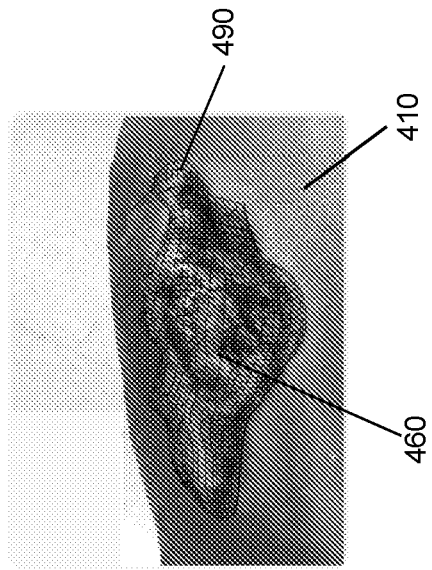
FIG. 37 is a photograph of a wound topology measured in accordance with the present disclosure.
Figure 36B:
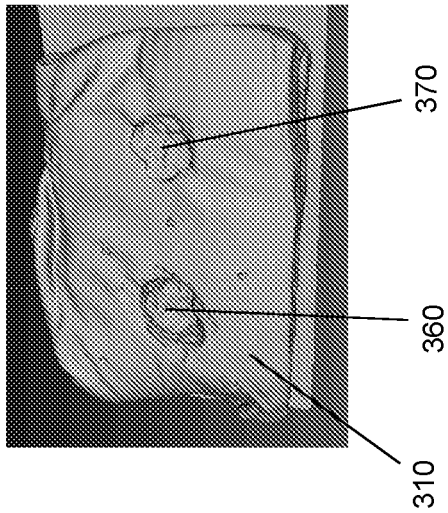
FIG. 36B is an image of the third tissue phantom undergoing a CT scan.

FIG. 35A is an image of the third tissue phantom 310 prepared with CT fiducial markers for a cone beam CT scan. FIG. 35B is a cone beam CT scan image of the third tissue phantom 310. FIG. 35C is an image of the third tissue phantom 310 prepared for a cone beam CT scan in a CT machine 380. FIG. 35D is an image of the third tissue phantom 310 undergoing a cone beam CT scan. FIG. 36A is an image of the third tissue phantom 310 prepared with CT fiducials 340 spatially co-registered with fluorescein fiducials 330 for a CT scan. FIG. 36B is an image of the third tissue phantom 310 undergoing a CT scan. FIG. 37 is a photograph superimposed with a wound topology grid 490 of a wound 460 on a skin 410 measured in accordance with the present disclosure. The measurement determined a length of about 4 cm, a width of about 9 cm, a depth of about 3 cm, and a volume of about 99.5 cm$^3$.

These figures show the ability of the techniques of the present disclosure to create three-dimensional images of tissues and other objects that serve as valuable tools for better characterizing and understanding the tissues and other objects. A physician, for example, can be better visualize the nature of a patient wound and its progression over time to help determine if a treatment regimen is effective or needs to be modified to promote wound healing. In addition, a physician can better visualize the location or size of an infection (or the location/quantity of bacteria present) in a wound and adapt treatment regimens accordingly. Thus, Example 3 demonstrates the effectiveness of the disclosed techniques.

The present disclosure includes the following aspects/embodiments/features in any order and/or in any combination:

A method of generating a three-dimensional image of a target using two-dimensional images, comprising: generating a three-dimensional map of a target area associated with one or more fiducial markers; capturing a two-dimensional white light image of the target area and the one or more fiducial markers; creating a three-dimensional white light image from the two-dimensional white light image and the three-dimensional map; capturing a two-dimensional fluorescence image of the target area and the one or more fiducial markers; creating a three-dimensional fluorescence image from the two-dimensional fluorescence image and the three-dimensional map; and aligning the three-dimensional white light image and the three-dimensional fluorescence image using the one or more fiducial markers to form a three-dimensional superimposed image.

2. The method of any preceding or following embodiment/feature/aspect, wherein the capturing of the two-dimensional fluorescence image of the target area and the one or more fiducial markers comprises: illuminating the target area and the one or more fiducial markers with an excitation light, and receiving at least one fluorescence emission responsive to illumination of the target area with the excitation light.

3. The method of any preceding or following embodiment/feature/aspect, wherein the excitation light is between about 400 nm and about 450 nm.

4. The method of any preceding or following embodiment/feature/aspect, wherein the excitation light has a wavelength of about 405 nm.

5. The method of any preceding or following embodiment/feature/aspect, wherein the capturing of the two-dimensional fluorescence image of the target area and the one or more fiducial markers comprises capturing an emission of at least one fluorescent molecule.

6. The method of any preceding or following embodiment/feature/aspect, wherein the at least one fluorescent molecule comprises an endogenous molecule capable of fluorescing.

7. The method of any preceding or following embodiment/feature/aspect, wherein the at least one fluorescent molecule comprises an exogenous molecule capable of fluorescing or a molecule comprising an exogenously added moiety capable of fluorescing.

8. The method of any preceding or following embodiment/feature/aspect, wherein the at least one fluorescent molecule comprises aminolevulinic acid (ALA) induced porphyrins.

9. The method of any preceding or following embodiment/feature/aspect, wherein the three-dimensional map is generated using infrared light.

10. The method of any preceding or following embodiment/feature/aspect, wherein the three-dimensional map is generated using near infrared light.

11. The method of any preceding or following embodiment/feature/aspect, wherein generating the three-dimensional map comprises: projecting infrared radiation at the target area; receiving infrared radiation reflected by the target area; and measuring depth of the target area based on the reflected infrared radiation to generate the three-dimensional map.

12. The method of any preceding or following embodiment/feature/aspect, wherein the infrared radiation is projected as a beam split into a light pattern, the reflected infrared radiation comprises a distortion of the light pattern, and the depth is measured based on the distortion of the light pattern.

13. The method of any preceding or following embodiment/feature/aspect, wherein the light pattern is formed by a diffraction grating and the light pattern comprises a plurality of dots.

14. The method of any preceding or following embodiment/feature/aspect, wherein the depth is measured by time-of-flight based on a phase shift between the projected and the reflected infrared radiation.

15. The method of any preceding or following embodiment/feature/aspect, wherein the target area comprises at least one wound.

16. The method of any preceding or following embodiment/feature/aspect, wherein the wound comprises at least one bacterium comprising at least one fluorescent molecule.

17. The method of any preceding or following embodiment/feature/aspect, wherein the method further comprises determining one or both of a surface area and a volume of the wound.

18. The method of any preceding or following embodiment/feature/aspect, wherein the method is performed at least twice, the two performances comprising a first performance and a second performance separated by a time period of at least three hours, the three-dimensional superimposed image of the first performance being a first three-dimensional superimposed image and the three-dimensional superimposed image of the second performance being a second three-dimensional superimposed image, the method further comprising comparing the first and second three-dimensional superimposed images to determine a wound healing status.

19. The method of any preceding or following embodiment/feature/aspect, wherein the time period is at least one day.

20. The method of any preceding or following embodiment/feature/aspect, wherein the wound healing status comprises a wound deterioration and the method further comprises administering at least one wound amelioration aid.

21. The method of any preceding or following embodiment/feature/aspect, wherein the comparison further comprises tracking a topography of the wound.

22. The method of any preceding or following embodiment/feature/aspect, wherein the target area comprises a tissue excised from a subject organism.

23. The method of any preceding or following embodiment/feature/aspect, wherein the tissue comprises a cancerous tissue.

24. The method of any preceding or following embodiment/feature/aspect, wherein the cancerous tissue comprises a tumor.

25. The method of any preceding or following embodiment/feature/aspect, wherein the tumor is a breast tumor and the excised tissue comprises a lumpectomy.

26. The method of any preceding or following embodiment/feature/aspect, wherein the excised tissue comprises a fluorescent molecule associated with a probe targeting a tumor receptor, an enzyme-activated fluorescent molecule, or a genetically modified oncolytic virus-induced fluorescence, or any combination thereof.
27. The method of any preceding or following embodiment/feature/aspect, wherein the tumor receptor comprises HER2, a folate receptor, CXCR4, a hormone receptor, an EGFR, or a VEGF, or a combination thereof; and the enzyme comprises a protease, a carbohydrase, a lipase, a transferase, an oxidoreductase, a matrix metalloprotease (MMP), a caspase, a cathepsin, a kallikrein, serine protease, isocitrate dehydrogenase, or an enzyme overexpressed by tumor cells, or a combination thereof.
28. The method of any preceding or following embodiment/feature/aspect, wherein target area comprises a surgical bed from which a tissue has been excised.
29. The method of any preceding or following embodiment/feature/aspect, wherein the surgical bed and the excised tissue comprises a cancerous tissue.
30. The method of any preceding or following embodiment/feature/aspect, wherein the method is performed at least twice, in either order, the two performances comprising a first performance and a second performance, the first performance performed on the target area, the target area being a first target area comprising an excised tissue, the second performance performed on a second target area comprising a surgical bed from which the tissue is excised, the three-dimensional superimposed image of the first performance being a first three-dimensional superimposed image and the three-dimensional superimposed image of the second performance being a second three-dimensional superimposed image, the method further comprising comparing the first and second three-dimensional superimposed images to determine a fluorescent continuity between the excised tissue and the surgical bed based on an orientation of the excised tissue relative to the surgical bed.
31. The method of any preceding or following embodiment/feature/aspect, wherein the fluorescent continuity comprises one or more of a bacterially infected tissue, a virally infected tissue, a burn, a cancerous tissue, a connective tissue, a muscle tissue, a blood vesicle, and a skin feature.
32. The method of any preceding or following embodiment/feature/aspect, wherein the fluorescent continuity corresponds to a compromised tissue and the method further comprises excising at least a portion of the compromised tissue from the surgical bed.
33. The method of any preceding or following embodiment/feature/aspect, further comprising: capturing a companion three-dimensional image of the target area and the one or more fiducial markers using an imaging technique comprising one or more of computerized tomography (CT), magnetic resonance imaging (MRI), photoacoustic imaging, ultrasound, and optical coherence tomography; and superimposing the three-dimensional superimposed image, the superimposed image being a first three-dimensional superimposed image, with the companion three-dimensional image to form a second three-dimensional superimposed image.
34. The method of any preceding or following embodiment/feature/aspect, wherein the one or more fiducial markers comprise a first set of fiducial markers and a second set of fiducial markers.
35. The method of any preceding or following embodiment/feature/aspect, wherein the companion three-dimensional image is captured using computerized tomography and the one or more fiducial markers comprise at least one fluorescent molecule and at least one CT contrast agent.
36. The method of any preceding or following embodiment/feature/aspect, wherein the companion three-dimensional image is captured using photoacoustic imaging, and the target area comprises a breast tumor and an anti-HER2 dual fluorescence-photoacoustic probe.
37. An imaging device comprising: an excitation light source configured to emit a first radiation capable of exciting a fluorophore; a filter configured to prevent passage of reflected excitation light and permit passage of fluorescence emitted by the fluorophore; an imaging lens; a visible light source configured to emit a second radiation; an infrared light source configured to emit a third radiation; at least one image sensor configured to detect radiation; and a processor configured to receive the detected radiation and to output data associated with the detected radiation.
38. The imaging device of any preceding or following embodiment/feature/aspect, wherein the imaging device is configured to be handheld.
39. The imaging device of any preceding or following embodiment/feature/aspect, wherein the imaging device is configured to visualize a wound.
40. The imaging device of any preceding or following embodiment/feature/aspect, wherein the imaging device is configured to visualize one or more of a precancerous cell, a cancerous cell, and a satellite lesion in a surgical margin.
41. The imaging device of any preceding or following embodiment/feature/aspect, wherein the excitation light source is further configured to excite autofluorescence emissions of tissue cells and fluorescence emissions of induced porphyrins in tissue cells of the surgical margin.
42. The imaging device of any preceding or following embodiment/feature/aspect, wherein the filter is further configured to prevent passage of reflected excitation light and permit passage of emissions having a wavelength corresponding to the autofluorescence emissions of the tissue cells and the fluorescence emissions of the induced porphyrins in the tissue cells.
43. The imaging device of any preceding or following embodiment/feature/aspect, wherein the image sensor is further configured to detect the filtered autofluorescence emissions of the tissue cells and the fluorescence emissions of the induced porphyrins in the tissue cells of the surgical margin.
44. The imaging device of any preceding or following embodiment/feature/aspect, wherein the processor is further configured to receive the detected emissions and to output data regarding the detected filtered autofluorescence emissions of the tissue cells and the fluorescence emissions of the induced porphyrins in the tissue cells of the surgical margin.
45. The imaging device of any preceding or following embodiment/feature/aspect, wherein the second radiation comprises white light.
46. The imaging device of any preceding or following embodiment/feature/aspect, wherein the second radiation comprises monochromatic visible light.
47. The imaging device of any preceding or following embodiment/feature/aspect, wherein the third radiation comprises infrared radiation.

48. The imaging device of any preceding or following embodiment/feature/aspect, wherein the infrared radiation comprises near infrared radiation.
49. The imaging device of any preceding or following embodiment/feature/aspect, wherein the at least one image sensor is configured to detect radiation comprising the fluorescence, reflected white light, and reflected infrared light
50. The imaging device of any preceding or following embodiment/feature/aspect, wherein the at least one sensor comprises at least two sensors.
51. The imaging device of any preceding or following embodiment/feature/aspect, wherein the at least two sensors comprise a first sensor configured to detect fluorescence and a second detector configured to detect reflected visible light.
52. The imaging device of any preceding or following embodiment/feature/aspect, wherein the at least one sensor comprises at least three sensors comprising a first sensor configured to detect fluorescence, a second detector configured to detect reflected visible light, and a third sensor configured to detect reflected infrared light.
53. The imaging device of any preceding or following embodiment/feature/aspect, further comprising a common radiation source configured to operate with at least one of the light sources.
54. The imaging device of any preceding or following embodiment/feature/aspect, wherein the at least one light source comprises a converter to convert source radiation emitted from the common radiation source to the first radiation, the second radiation, or the third radiation, or a combination thereof.
55. The imaging device of any preceding or following embodiment/feature/aspect, wherein the converter comprises a filter, a lens, a prism, a diffractor, or a quantum dot, or a combination thereof.
56 The imaging device of any preceding or following embodiment/feature/aspect, wherein the excitation light source comprises a first converter, the visible light source comprises a second converter, and the infrared light source comprises a third converter.
57. The imaging device of any preceding or following embodiment/feature/aspect, further comprising a display unit.
58. The imaging device of any preceding or following embodiment/feature/aspect, wherein the display unit is configured to display the data output by the processor.
59. The imaging device of any preceding or following embodiment/feature/aspect, wherein the data comprises a three-dimensional image.
60. The imaging device of any preceding or following embodiment/feature/aspect, wherein the display unit comprises a touchscreen.
61. The imaging device of any preceding or following embodiment/feature/aspect, wherein the detected radiation comprises one or more of fluorescence, reflected visible light, and reflected infrared light.
62. The imaging device of any preceding or following embodiment/feature/aspect, wherein the detected radiation comprises fluorescence, reflected visible light, and reflected infrared light.
63. The imaging device of any preceding or following embodiment/feature/aspect, wherein the imaging device is configured to visualize a target area of a biological target.
64. The imaging device of any preceding or following embodiment/feature/aspect, wherein the processor is further configured to generate a three-dimensional map of the target area.
65. The imaging device of any preceding or following embodiment/feature/aspect, wherein the three-dimensional map is generated from infrared light reflected from the target area.
66. The imaging device of any preceding or following embodiment/feature/aspect, wherein the processor is further configured to capture a two-dimensional visible light image of the target area based on the detected radiation.
67. The imaging device of any preceding or following embodiment/feature/aspect, wherein the processor is further configured to create a three-dimensional visible light image of the target area based on the three-dimensional map and the two-dimensional visible light image.
68. The imaging device of any preceding or following embodiment/feature/aspect, wherein the processor is further configured to capture a two-dimensional fluorescence image of the target area based on the detected radiation.
69. The imaging device of any preceding or following embodiment/feature/aspect, wherein the processor is further configured to create a three-dimensional fluorescence image of the target area based on the three-dimensional map and the two-dimensional fluorescence image.
70. The imaging device of any preceding or following embodiment/feature/aspect, wherein the processor is further configured to align a three-dimensional visible light image of the target area with a three-dimensional fluorescence image of the target area to form a three-dimensional superimposed image of the target area.
71. The imaging device of any preceding or following embodiment/feature/aspect, wherein the alignment is performed based on co-registration of fiducial markers associated with the target area.
72. The imaging device of any preceding or following embodiment/feature/aspect, wherein the imaging device is configured to perform the method of any preceding or following embodiment/feature/aspect.
73. The imaging device of any preceding or following embodiment/feature/aspect, wherein: the imaging device is further configured to be handheld; the excitation light source is further configured to excite autofluorescence emissions of tissue cells and fluorescence emissions having a wavelength of between about 600 nm and about 660 nm in precancerous cells, cancerous cells, and satellite lesions of a surgical margin after exposure to an imaging or contrast agent; the filter is further configured to permit passage of emissions having a wavelength corresponding to autofluorescence emissions of the tissue cells and fluorescence emissions between about 600 nm and about 660 nm in the tissue cells of the surgical margin; the at least one image sensor is further configured to detect the filtered autofluorescence emissions of the tissue cells and the fluorescence emissions between about 600 nm and about 660 nm in the tissue cells of the surgical margin; and the processor is further configured to receive the detected emissions and to output data regarding the detected filtered autofluorescence emissions of the tissue cells and the fluorescence emissions between about 600 nm and about 660 nm in the tissue cells of the surgical margin, and to generate a three-dimensional image of one or more of the precancerous cells, the cancerous cells, and the satellite lesions in the surgical margins.

74. A system for three-dimensional fluorescence-based imaging of a target, comprising: at least one excitation light source configured to uniformly illuminate a target surface with a uniform field of excitation light during fluorescent imaging; at least one white-light source configured to illuminate the target surface during white light imaging; at least one infrared radiation source configured to emit infrared radiation toward the target surface; an image sensor; a filter configured to permit optical signals responsive to illumination of the target surface with the excitation light and having a wavelength corresponding to one or more of bacterial autofluorescence and tissue autofluorescence to pass through the filter to the image sensor; and a processor configured to: receive optical signals responsive to illumination of the target with the infrared light and, based on the received signals responsive to illumination of the target with the infrared light, generate a three-dimensional map of the target surface, receive detected optical signals responsive to illumination of the target surface with excitation light and generate a two-dimensional fluorescence image of the target surface, receive optical signals responsive to white light illumination of the target surface and generate a two-dimensional white light image of the target surface, and combine the three-dimensional map, the fluorescence image, and the white light image to generate a three-dimensional image of the target surface.

75. A computer program product for use with the imaging device of any preceding or following embodiment/feature/aspect, the computer program product comprising a non-transitory computer readable medium, wherein the non-transitory computer readable medium stores a computer program code for image processing, wherein the computer program code is executable by the processor in the imaging device to perform the method of any preceding or following embodiment/feature/aspect.

Other embodiments will be apparent to those skilled in the art from consideration of the specification and practice of the present disclosure disclosed herein. It is intended that the specification and examples be considered as exemplary only. Various aspects of the disclosure are set forth in the following claims.

What is claimed is:

1. An imaging device comprising:
an excitation light source configured to emit a first radiation capable of exciting a fluorophore in a target area;
a filter configured to prevent passage of reflected excitation light from the target area and permit passage of fluorescence emitted by the fluorophore;
an imaging lens;
a visible light source configured to emit a second radiation;
an infrared light source configured to emit a third radiation;
at least one image sensor configured to detect radiation emitted from the target area; and
a processor configured to receive the detected radiation and to output data associated with the detected radiation,
wherein the processor is further configured to execute:
generating a three-dimensional map of the target area, wherein the three-dimensional map is generated using infrared light reflected from the target area;
capturing a two-dimensional visible light image of the target area;
creating a three-dimensional visible light image from the two-dimensional visible light image and the three-dimensional map;
capturing a two-dimensional fluorescence image of the target area;
creating a three-dimensional fluorescence image from the two-dimensional fluorescence image and the three-dimensional map; and
aligning the three-dimensional visible light image and the three-dimensional fluorescence image of the target area to form a three-dimensional superimposed image of the target area.

2. The imaging device of claim 1, wherein the imaging device is configured to be handheld.

3. The imaging device of claim 1, wherein the imaging device is configured to visualize a wound.

4. The imaging device of claim 1, wherein the imaging device is configured to visualize one or more of a precancerous cell, a cancerous cell, and a satellite lesion in a surgical margin.

5. The imaging device of claim 4, wherein the excitation light source is further configured to excite autofluorescence emissions of tissue cells and fluorescence emissions of induced porphyrins in tissue cells of the surgical margin.

6. The imaging device of claim 5, wherein the filter is further configured to prevent passage of reflected excitation light and permit passage of emissions having a wavelength corresponding to the autofluorescence emissions of the tissue cells and the fluorescence emissions of the induced porphyrins in the tissue cells.

7. The imaging device of claim 6, wherein the image sensor is further configured to detect the filtered autofluorescence emissions of the tissue cells and the fluorescence emissions of the induced porphyrins in the tissue cells of the surgical margin.

8. The imaging device of claim 7, wherein the processor is further configured to receive the detected emissions and to output data regarding the detected filtered autofluorescence emissions of the tissue cells and the fluorescence emissions of the induced porphyrins in the tissue cells of the surgical margin.

9. The imaging device of claim 1, wherein the second radiation comprises white light.

10. The imaging device of claim 1, wherein the second radiation comprises monochromatic visible light.

11. The imaging device of claim 1, wherein the third radiation comprises infrared radiation.

12. The imaging device of claim 11, wherein the infrared radiation comprises near infrared radiation.

13. The imaging device of claim 1, wherein the at least one image sensor is configured to detect radiation comprising the fluorescence, reflected white light, and reflected infrared light.

14. The imaging device of claim 1, wherein the at least one sensor comprises at least two sensors.

15. The imaging device of claim 14, wherein the at least two sensors comprise a first sensor configured to detect fluorescence and a second detector configured to detect reflected visible light.

16. The imaging device of claim 1, wherein the at least one sensor comprises at least three sensors comprising a first sensor configured to detect fluorescence, a second detector configured to detect reflected visible light, and a third sensor configured to detect reflected infrared light.

17. The imaging device of claim 1, further comprising a common radiation source configured to operate with at least one of the light sources.

18. The imaging device of claim 17, wherein the at least one light source comprises a converter to convert source radiation emitted from the common radiation source to the first radiation, the second radiation, or the third radiation, or a combination thereof.

19. The imaging device of claim 18, wherein the converter comprises a filter, a lens, a prism, a diffractor, or a quantum dot, or a combination thereof.

20. The imaging device of claim 18, wherein the excitation light source comprises a first converter, the visible light source comprises a second converter, and the infrared light source comprises a third converter.

21. The imaging device of claim 1, further comprising a display unit.

22. The imaging device of claim 21, wherein the display unit is configured to display the data output by the processor.

23. The imaging device of claim 21, wherein the data comprises a three-dimensional image.

24. The imaging device of claim 21, wherein the display unit comprises a touchscreen.

25. The imaging device of claim 1, wherein the detected radiation comprises one or more of fluorescence, reflected visible light, and reflected infrared light.

26. The imaging device of claim 1, wherein the detected radiation comprises fluorescence, reflected visible light, and reflected infrared light.

27. The imaging device of claim 1, wherein the imaging device is configured to visualize a target area of a biological target.

28. The imaging device of claim 1, wherein the alignment is performed based on co-registration of fiducial markers associated with the target area.

29. The imaging device of claim 1, wherein:
the imaging device is further configured to be handheld;
the excitation light source is further configured to excite autofluorescence emissions of tissue cells and fluorescence emissions having a wavelength of between about 600 nm and about 660 nm in precancerous cells, cancerous cells, and satellite lesions of a surgical margin after exposure to an imaging or contrast agent;
the filter is further configured to permit passage of emissions having a wavelength corresponding to autofluorescence emissions of the tissue cells and fluorescence emissions between about 600 nm and about 660 nm in the tissue cells of the surgical margin;
the at least one image sensor is further configured to detect the filtered autofluorescence emissions of the tissue cells and the fluorescence emissions between about 600 nm and about 660 nm in the tissue cells of the surgical margin; and
the processor is further configured to receive the detected emissions and to output data regarding the detected filtered autofluorescence emissions of the tissue cells and the fluorescence emissions between about 600 nm and about 660 nm in the tissue cells of the surgical margin, and to generate a three-dimensional image of one or more of the precancerous cells, the cancerous cells, and the satellite lesions in the surgical margins.

30. A computer program product for use with the imaging device of claim 1, the computer program product comprising a non-transitory computer readable medium, wherein the non-transitory computer readable medium stores a computer program code for image processing, wherein the computer program code is executable by the processor in the imaging device.

* * * * *